(12) United States Patent
Lauber et al.

(10) Patent No.: US 12,048,926 B2
(45) Date of Patent: Jul. 30, 2024

(54) COATINGS WITH IMMOBILIZED AFFINITY LIGANDS AND ENZYMES AND USE THEREOF IN LIQUID CHROMATOGRAPHY ASSAYS

(71) Applicant: Waters Technologies Corporation, Milford, MA (US)

(72) Inventors: Matthew A. Lauber, North Smithfield, RI (US); Mathew H. DeLano, Needham, MA (US); Beatrice Muriithi, Attleboro, MA (US); Xiaoxiao Liu, Natick, MA (US); Anna Boardman, Watertown, MA (US)

(73) Assignee: Waters Technologies Corporation, Milford, MA (US)

( * ) Notice: Subject to any disclaimer, the term of this patent is extended or adjusted under 35 U.S.C. 154(b) by 779 days.

(21) Appl. No.: 16/913,393

(22) Filed: Jun. 26, 2020

(65) Prior Publication Data
US 2020/0406252 A1 Dec. 31, 2020

Related U.S. Application Data

(60) Provisional application No. 62/866,847, filed on Jun. 26, 2019.

(51) Int. Cl.
*B01L 3/00* (2006.01)
*B01D 15/38* (2006.01)
*B01D 15/42* (2006.01)

(52) U.S. Cl.
CPC ........ *B01L 3/5023* (2013.01); *B01D 15/3809* (2013.01); *B01D 15/424* (2013.01);
(Continued)

(58) Field of Classification Search
CPC .......... B01L 3/5023; B01L 2200/0631; B01L 2200/0668; B01L 2300/0681;
(Continued)

(56) References Cited

U.S. PATENT DOCUMENTS 4,560,504 A * 12/1985 Arnold ................ B01J 20/3257
435/948
2003/0138973 A1 7/2003 Wagner et al.
(Continued)

FOREIGN PATENT DOCUMENTS

| WO | 2006008143 A2 | 1/2006 |
| WO | 2012170755 A1 | 12/2012 |
| WO | 2019053693 A1 | 3/2019 |

OTHER PUBLICATIONS

Schomburg et al., "Immobilization of Stationary Liquids in Reversed and Normal-Phase Liquid Chromatography", Journal of Chromatography, 282 (1983) pp. 27-39. (Year: 1983).*
(Continued)

*Primary Examiner* — Rebecca M Giere
(74) *Attorney, Agent, or Firm* — WOMBLE BOND DICKINSON (US) LLP; Deborah M. Vernon; Matthew J. Powers

(57) ABSTRACT

A sample preparation device is provided for enriching a component of a sample. The sample preparation device includes a surface in fluid communication with the sample, an alkylsilyl coating disposed on the surface, and an affinity ligand or an enzyme covalently bonded to the alkylsilyl coating.

16 Claims, 7 Drawing Sheets

Specification includes a Sequence Listing.

(52) U.S. Cl.
CPC .......... *B01L 2200/0631* (2013.01); *B01L 2200/0668* (2013.01); *B01L 2300/0681* (2013.01); *B01L 2300/069* (2013.01); *B01L 2400/0409* (2013.01); *B01L 2400/0433* (2013.01)

(58) Field of Classification Search
CPC ....... B01L 2300/069; B01L 2400/0409; B01L 2400/0433; B01L 3/50255; B01L 3/02; B01L 3/50; B01D 15/3809; B01D 15/424; B01D 15/12; B01D 15/3804; C07K 1/22; G01N 2030/062; G01N 2030/085; G01N 30/02; G01N 30/08; G01N 30/72; G01N 2030/027
See application file for complete search history.

(56) References Cited

U.S. PATENT DOCUMENTS

| | | | | |
|---|---|---|---|---|
| 2007/0092867 A1* | 4/2007 | Kim | ............... | B82Y 15/00 435/7.1 |
| 2009/0206034 A1* | 8/2009 | Nakajima | ............ | B01J 20/3276 528/34 |
| 2014/0162298 A1* | 6/2014 | Ahn | ............... | C12Q 1/48 435/23 |

OTHER PUBLICATIONS

Invitation to Pay Additional Fees and, Where Appliable, Protest Fee issued in International Application No. PCT/IB2020/056087 dated Sep. 21, 2020.

\* cited by examiner

| COATING # | DEPOSITED MATERIAL | ALTERNATIVE COATING ABBREVIATION | ALKYL SILYL COATING REAGENT | CHARGE MODIFIER (R^C) REAGENT | HYDROPHOBICITY MODIFIER (R^B) REAGENT |
|---|---|---|---|---|---|
| 1 | BIS(TRICHLOROSILYL)ETHANE FOLLOWED BY TRIMETHOXY SILYL PROPYL METHYL PHOSPHONATE | C2-PHOSPHONATE | 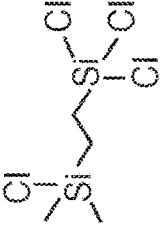 |  | N/A |
| 2 | BIS(TRICHLOROSILYL)ETHANE FOLLOWED BY TRIMETHOXY SILYL PROPYL METHYL PHOSPHONATE FOLLOWED BY n-DECYL TRICHLOROSILANE | C2-PHOSPHONATE-C10 |  | 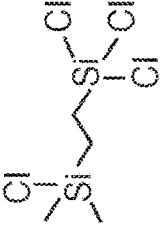 |  |
| 3 | BIS(TRICHLOROSILYL)ETHANE FOLLOWED BY N,N-(DIETHYLAMINOPROPYL) TRIMETHOXYSILANE | C2-DEAP |  | 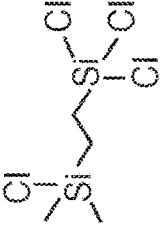 | N/A |
| 4 | BIS(TRICHLOROSILYL)ETHANE FOLLOWED BY N,N-(DIETHYLAMINOPROPYL) TRIMETHOXYSILANE FOLLOWED BY n-DECYL TRICHLOROSILANE | C2-DEAP-C10 |  |  | 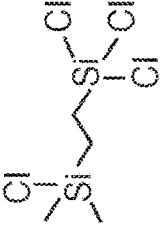 |
| 5 | BIS(TRICHLOROSILYL)ETHANE FOLLOWED BY N,N-(DIETHYLAMINOPROPYL) TRIMETHOXYSILANE FOLLOWED BY N-(3-TRIETHOXYSILYLPROPYL) GLUCONAMIDE | C2-DEAP-GLUCO |  |  | 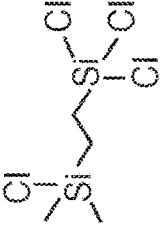 |

| # | DEPOSITED/IMMOBILIZED MATERIALS | ABBREVIATION | FORMULA I |
|---|---|---|---|
| 1 | BIS(TRICHLOROSILYL)ETHANE, 3-AMINOPROPYL TRIMETHOXY SILANE, NHS PEG MALEIMIDE, ANTI-HUMAN FC VHH | $C_2$-AMIDEPEG MALEIMIDE-ANTI FC | 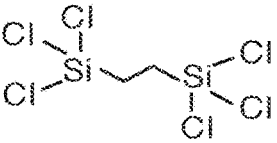 |
| 2 | BIS(TRICHLOROSILYL)ETHANE, TRIETHOXYSILYL BUTYRALDEHYDE, ANTI-HUMAN FC VHH | $C_2$-RED-ANTI FC | 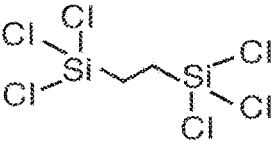 |
| 3 | BIS(TRICHLOROSILYL)ETHANE, 3-AMINOPROPYL TRIMETHOXY SILANE, SULFOBETAINE TRIMETHOXY SILANE, NHS PEG MALEIMIDE, ANTI-HUMAN FC VHH | $C_2$-AMIDEPEG MALEIMIDE-BETAINE- ANTI FC | 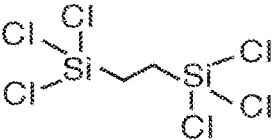 |
| 4 | BIS(TRICHLOROSILYL)ETHANE, 3-AMINOPROPYL TRIMETHOXY SILANE, N-(3-TRIETHOXYSILYLPROPYL), GLUCONAMIDE, ANTI-HUMAN FC VHH | $C_2$-RED-HYDROXY-ANTI FC | 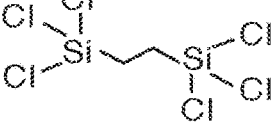 |
| 5 | BIS(TRICHLOROSILYL)ETHANE, PEG MALEIMIDE SILANE, TRYPSIN | $C_2$-PEG-TRYPSIN | 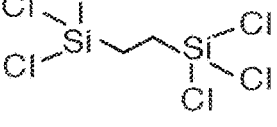 |
| 6 | BIS(TRICHLOROSILYL)ETHANE, TRIETHOXYSILYL BUTYRALDEHYDE, TRYPSIN | $C_2$-RED-TRYPSIN | 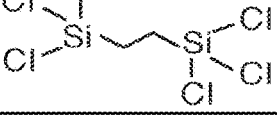 |
| 7 | BIS(TRICHLOROSILYL)ETHANE, 3-AMINOPROPYL TRIMETHOXY SILANE, PEG DIALEDEHYDE TRYPSIN | $C_2$-RED-PEG-TRYPSIN | 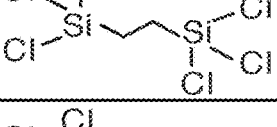 |
| 8 | BIS(TRICHLOROSILYL)ETHANE, TRIETHOXYSILYL BUTYRALDEHYDE, ACRYLATE, PEG AMINE, TRYPSIN | $C_2$-RED-MICHPEG-TRYPSIN | 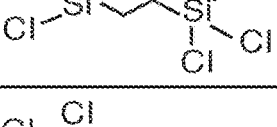 |
| 9 | BIS(TRICHLOROSILYL)ETHANE, ACRYLOXYPROPYLTRIMETHOXY, SILANE, TRYPSIN | $C_2$-ACRYLOXY-TRYPSIN | 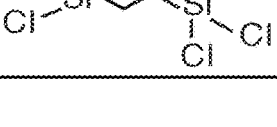 |

FIG. 5B

| # | FORMULA II | FORMULA III |
|---|---|---|
| 1 | (CH₃O)₃Si-(CH₂)₃-NH₂ | N/A |
| 2 | N/A | (EtO)₃Si-(CH₂)₃-CHO |
| 3 | (CH₃O)₃Si-(CH₂)₃-NH₂ | (CH₃O)₃Si-(CH₂)₃-N⁺(CH₃)-(CH₂)₃-SO₃⁻ |
| 4 | (CH₃O)₃Si-(CH₂)₃-NH₂ | (EtO)₃Si-(CH₂)₃-NH-C(O)-[CH(OH)]₄-CH₂OH (gluconamide) |
| 5 | N/A | N/A |
| 6 | N/A | (EtO)₃Si-(CH₂)₃-CHO |
| 7 | (CH₃O)₃Si-(CH₂)₃-NH₂ | N/A |
| 8 | (EtO)₃Si-(CH₂)₃-CHO | CH₂=CH-C(O)-O-(CH₂CH₂O)ₙ-NH₂ (PEG) |
| 9 | N/A | CH₂=CH-C(O)-O-(CH₂)₂-Si(OCH₃)₃ |

FIG. 5C

| # | LINKAGE | BIOLOGICAL LIGAND |
|---|---|---|
| 1 | [maleimide-(CH₂)₄-C(O)NH-CH₂CH₂-(O-CH₂CH₂)ₙ-O-CH₂CH₂-C(O)-O-NHS ester structure] | ANTI-HUMAN Fc VHH SINGLE DOMAIN ANTIBODY |
| 2 | REDUCTIVE AMINATION | ANTI-HUMAN Fc VHH SINGLE DOMAIN ANTIBODY |
| 3 | [maleimide-(CH₂)₄-C(O)NH-CH₂CH₂-(O-CH₂CH₂)ₙ-O-CH₂CH₂-C(O)-O-NHS ester structure] | ANTI-HUMAN Fc VHH SINGLE DOMAIN ANTIBODY |
| 4 | REDUCTIVE AMINATION WITH GLUTARALDEHYDE [OHC-(CH₂)₃-CHO structure] | ANTI-HUMAN Fc VHH SINGLE DOMAIN ANTIBODY |
| 5 | [maleimide-C(O)NH-CH₂CH₂-(CH₂CH₂O)ₙ-CH₂CH₂-NH-C(O)-NH-(CH₂)₃-Si(OEt)₃ structure] PEG | PORCINE TRYPSIN |
| 6 | REDUCTIVE AMINATION | PORCINE TRYPSIN |
| 7 | REDUCTIVE AMINATION WITH [OHC-CH₂CH₂-C(O)-O-(CH₂CH₂O)ₙ-CH₂CH₂-C(O)-CH₃ structure] | PORCINE TRYPSIN |
| 8 | REDUCTIVE AMINATION AND MICHAEL ADDITION | PORCINE TRYPSIN |
| 9 | MICHAEL ADDITION | PORCINE TRYPSIN |

SEQUENCE LISTING

<160> NUMBER OF SEQ ID NOS: 4

<210> SEQ ID NO 1
<211> LENGTH: 139
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 1

Gln Val Gln Leu Gln Glu Ser Gly Gly Gly Leu Val Gln Pro Gly Gly
1               5                   10                  15

Ser Leu Arg Ser Cys Ala Ala Ser Gly Gly Thr Ser Ile Arg Ile Gly
            20                  25                  30

```
Ser Ile Asn Ala Leu Ala Trp Tyr Arg Gln Ala Leu Gly Asn Gln Arg
        35                  40                  45

Glu Leu Val Ala Val Thr Glu Gly Gly Ser Thr Asn Tyr Ala Asp
 50                  55                  60

Phe Val Lys Gly Arg Phe Thr Ile Ser Arg Asp Gln Ala Gln Asn Met
 65                  70                  75                  80

Met Tyr Leu Gln Met Asn Ser Leu Lys Pro Glu Asp Thr Ala Val Tyr
                 85                  90                  95

Tyr Cys Asn Ala Asp Lys Val Leu Tyr Ser Arg Gly Tyr Tyr Ser
                100                 105                 110

Val Ala Asn Asp Leu Trp Gly Gln Gly Thr Gln Val Thr Val Ser Ser
        115                 120                 125

Gln Ala Pro Lys Val Asp Ala Lys Phe Asp Cys
    130                 135
```

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 2
ggaggugcuc cgaaaggaac ucc                                           23

<210> SEQ ID NO 3
<211> LENGTH: 223
<212> TYPE: PRT
<213> ORGANISM: Sus sp.

<400> SEQUENCE: 3

```
Ile Val Gly Gly Tyr Thr Cys Ala Ala Asn Ser Ile Pro Tyr Gln Val
 1               5                  10                  15

Ser Leu Asn Ser Gly Ser His Phe Cys Gly Gly Ser Leu Ile Asn Ser
            20                  25                  30

Gln Trp Val Val Ser Ala Ala His Cys Tyr Lys Ser Arg Ile Gln Val
        35                  40                  45

Arg Leu Gly Glu His Asn Ile Asp Val Leu Glu Gly Asn Glu Gln Phe
 50                  55                  60

Ile Asn Ala Ala Lys Ile Ile Thr His Pro Asn Phe Asn Gly Asn Thr
 65                  70                  75                  80

Leu Asp Asn Asp Ile Met Leu Ile Lys Leu Ser Ser Pro Ala Thr Leu
                 85                  90                  95

Asn Ser Arg Val Ala Thr Val Ser Leu Pro Arg Ser Cys Ala Ala Ala
                100                 105                 110

Gly Thr Glu Cys Leu Ile Ser Gly Trp Gly Asn Thr Lys Ser Ser Gly
        115                 120                 125

Ser Ser Tyr Pro Ser Leu Leu Gln Cys Leu Lys Ala Pro Val Leu Ser
    130                 135                 140

Asp Ser Ser Cys Lys Ser Ser Tyr Pro Gly Gln Ile Thr Gly Asn Met
145                 150                 155                 160

Ile Cys Val Gly Phe Leu Glu Gly Gly Lys Asp Ser Cys Gln Gly Asp
                165                 170                 175

Ser Gly Gly Pro Val Val Cys Asn Gly Gln Leu Gln Gly Ile Val Ser
```

```
                    180                 185                 190
Trp Gly Tyr Gly Cys Ala Gln Lys Asn Lys Pro Gly Val Tyr Thr Lys
            195                 200                 205

Val Cys Asn Tyr Val Asn Trp Ile Gln Gln Thr Ile Ala Ala Asn
210                 215                 220

<210> SEQ ID NO 4
<211> LENGTH: 630
<212> TYPE: PRT
<213> ORGANISM: Unknown
<220> FEATURE:
<223> OTHER INFORMATION: Description of Unknown:
      Beta-Glucuronidase sequence

<400> SEQUENCE: 4

Gly Leu Gln Gly Gly Met Leu Tyr Pro Gln Glu Ser Pro Ser Arg Glu
1               5                   10                  15

Cys Lys Glu Leu Asp Gly Leu Trp Ser Phe Arg Ala Asp Phe Ser Asp
            20                  25                  30

Asn Arg Arg Gly Phe Glu Glu Gln Trp Tyr Arg Arg Pro Leu Trp
        35                  40                  45

Glu Ser Gly Pro Thr Val Asp Met Pro Val Pro Ser Ser Phe Asn Asp
50                  55                  60

Ile Ser Gln Asp Trp Arg Leu Arg His Phe Val Gly Trp Val Trp Tyr
65                  70                  75                  80

Glu Arg Glu Val Ile Leu Pro Glu Arg Trp Thr Gln Asp Leu Arg Thr
                85                  90                  95

Arg Val Val Leu Arg Ile Gly Ser Ala His Ser Tyr Ala Ile Val Trp
            100                 105                 110

Val Asn Gly Val Asp Thr Leu Glu His Glu Gly Gly Tyr Leu Pro Phe
        115                 120                 125

Glu Ala Asp Ile Ser Asn Leu Val Gln Val Gly Pro Leu Pro Ser Arg
130                 135                 140

Leu Arg Ile Thr Ile Ala Ile Asn Asn Thr Leu Thr Pro Thr Thr Leu
145                 150                 155                 160

Pro Pro Gly Thr Ile Gln Tyr Leu Thr Asp Thr Ser Lys Tyr Pro Lys
                165                 170                 175

Gly Tyr Phe Val Gln Asn Thr Tyr Phe Asp Phe Phe Asn Tyr Ala Gly
            180                 185                 190

Leu Gln Arg Ser Val Leu Leu Tyr Thr Thr Pro Thr Thr Tyr Ile Asp
        195                 200                 205

Asp Ile Thr Val Thr Thr Ser Val Glu Gln Asp Ser Gly Leu Val Asn
210                 215                 220

Tyr Gln Ile Ser Val Lys Gly Ser Asn Leu Phe Lys Leu Glu Val Arg
225                 230                 235                 240

Leu Leu Asp Ala Glu Asn Lys Val Val Ala Asn Gly Thr Gly Thr Gln
                245                 250                 255

Gly Gln Leu Lys Val Pro Gly Val Ser Leu Trp Trp Pro Tyr Leu Met
            260                 265                 270

His Glu Arg Pro Ala Tyr Leu Tyr Ser Leu Glu Val Gln Leu Thr Ala
        275                 280                 285

Gln Thr Ser Leu Gly Pro Val Ser Asp Phe Tyr Thr Leu Pro Val Gly
        290                 295                 300

Ile Arg Thr Val Ala Val Thr Lys Ser Gln Phe Leu Ile Asn Gly Lys
305                 310                 315                 320
```

-continued

```
Pro Phe Tyr Phe His Gly Val Asn Lys His Glu Asp Ala Asp Ile Arg
                325                 330                 335

Gly Lys Gly Phe Asp Trp Pro Leu Leu Val Lys Asp Phe Asn Leu Leu
            340                 345                 350

Arg Trp Leu Gly Ala Asn Ala Phe Arg Thr Ser His Tyr Pro Tyr Ala
        355                 360                 365

Glu Glu Val Met Gln Met Cys Asp Arg Tyr Gly Ile Val Val Ile Asp
    370                 375                 380

Glu Cys Pro Gly Val Gly Leu Ala Leu Pro Gln Phe Phe Asn Asn Val
385                 390                 395                 400

Ser Leu His His His Met Gln Val Met Glu Glu Val Val Arg Arg Asp
                405                 410                 415

Lys Asn His Pro Ala Val Val Met Trp Ser Val Ala Asn Glu Pro Ala
            420                 425                 430

Ser His Leu Glu Ser Ala Gly Tyr Tyr Leu Lys Met Val Ile Ala His
        435                 440                 445

Thr Lys Ser Leu Asp Pro Ser Arg Pro Val Thr Phe Val Ser Asn Ser
    450                 455                 460

Asn Tyr Ala Ala Asp Lys Gly Ala Pro Tyr Val Asp Val Ile Cys Leu
465                 470                 475                 480

Asn Ser Tyr Tyr Ser Trp Tyr His Asp Tyr Gly His Leu Glu Leu Ile
                485                 490                 495

Gln Leu Gln Leu Ala Thr Gln Phe Glu Asn Trp Tyr Lys Lys Tyr Gln
            500                 505                 510

Lys Pro Ile Ile Gln Ser Glu Tyr Gly Ala Glu Thr Ile Ala Gly Phe
        515                 520                 525

His Gln Asp Pro Pro Leu Met Phe Thr Glu Glu Tyr Gln Lys Ser Leu
    530                 535                 540

Leu Glu Gln Tyr His Leu Gly Leu Asp Gln Lys Arg Arg Lys Tyr Val
545                 550                 555                 560

Val Gly Glu Leu Ile Trp Asn Phe Ala Asp Phe Met Thr Glu Gln Ser
                565                 570                 575

Pro Thr Arg Val Leu Gly Asn Lys Lys Gly Ile Phe Thr Arg Gln Arg
            580                 585                 590

Gln Pro Lys Ser Ala Ala Phe Leu Leu Arg Glu Arg Tyr Trp Lys Ile
        595                 600                 605

Ala Asn Glu Thr Arg Tyr Pro His Ser Val Ala Lys Ser Gln Cys Leu
    610                 615                 620

Glu Asn Ser Leu Phe Thr
625                 630
```

COATINGS WITH IMMOBILIZED AFFINITY LIGANDS AND ENZYMES AND USE THEREOF IN LIQUID CHROMATOGRAPHY ASSAYS

CROSS-REFERENCE TO RELATED APPLICATIONS

This application claims priority to and benefit of U.S. provisional patent application No. 62/866,847 filed on Jun. 26, 2019 and entitled "Coatings With Immobilized Affinity Ligands and Enzymes and Use Thereof in Liquid Chromatography Assays," the entire contents of which is hereby incorporated by reference.

SEQUENCE LISTING

The instant application contains a Sequence Listing which has been submitted electronically in ASCII format and is hereby incorporated by reference herein in its entirety. Said ASCII copy, created on Jun. 24, 2020, is named W-4064-US02_(102994_1013_4)_SL.txt and is 10 kilobytes in size.

FIELD OF THE TECHNOLOGY

The present disclosure relates to sample preparation devices and methods for enriching a component of a sample. More specifically, the present technology relates to a sample preparation device having an alkylsilyl coating with an affinity ligand or an enzyme covalently bonded to the alkylsilyl coating and methods of enriching a component (e.g., an analyte) of a sample using the sample preparation devices described herein.

BACKGROUND

Liquid chromatography (LC) systems are used to carry out chemical separations. A typical liquid chromatography system consists of the following major components: a pump, an injector, a column, and a detector. The pump compels a mobile phase, for example, a solution, through a fluid path comprising an injector, column and detector. The injector permits the introduction of samples into the fluid stream above the column. The column contains a packed bed of media. The media is normally porous and relatively inert. Compounds in the sample will exhibit a characteristic affinity to the media. That is, some compounds exhibit high affinity and some compounds exhibit low affinity. As a result, as the compounds are carried through the media, the compounds separate into bands which elute or come off the column at different times. These bands are detected by the detector.

When biological samples are being separated with liquid chromatography (LC) and detected with mass spectrometry (MS), it is sometimes necessary to enhance the selectivity and improve the limits of detection prior to introducing the sample to an LC-MS system. For example, a highly hydrophobic plastic plate, often referred to as a passive adsorption immunoassay plate, can be used. This style of plate adsorbs an affinity ligand through non-covalent interactions. Once activated with a ligand such as a protein, it can be used for sample processing or for immunosorbent sandwich assays, such as ELISA. Similarly, streptavidin immunoassay plates are available that can be used with biotinylated secondary ligands. These plates comprise immobilized streptavidin. Without being bound by theory, it is believed that the streptavidin immobilization is through activation and radical based polymerization off of polystyrene, polystyrene divinylbenzene, polycarbonate or polypropylene. In both cases, these types of plates have a noted disadvantage in their requirement for multiple intermolecular complexes to be formed to access the target analyte and that many applications require the use of blocking agents like polyethylene glycol sorbitan monolaurate. Moreover, they often do not exhibit ideal dynamic ranges, because of insufficient surface area, ligand coverage, and binding capacity.

Glygen Corporation has commercialized so-called NuTip devices (commercially available from GlySci a Glygen Corporation company, Columbia, Md.) which are fabricated with heat and pressure to have wall surfaces embedded with resin. Protein A and streptavidin affinity tips are available. See U.S. Pat. No. 6,416,716 as an example.

In addition, Corning® BioCoat™ labware (commercially available from Corning Incorporation, Corning, N.Y.) has been developed to facilitate culturing of adherent cell colonies. Sterile plastics modified to have polylysine surfaces are an example. In other instances, sterile plastics are coated with collagen or fibronectin.

Kellie and co-workers published methods for immunocapture that represent hybrid ligand binding assay/LC-MS approaches. As published in Bioanalysis (2016) 8(20), 2103-2114 entitled A Whole-Molecule Immunocapture LC-MS Approach for the in vivo Quantitation of Biotherapeutics, an adsorption immunoassay plate called the MaxiSorp NUNC polystyrene plate (commercial available from Thermo Fisher Scientific, Waltham, Mass.) was used to adsorb an anti-idiotypic antibody and thereafter pull down and quantify a biotherapeutic mAb by LC-MS. This plate is a product of Thermo Fisher Scientific, which has a portfolio of immunoassay plates, including passive adsorption, covalent linker activated supports, and immobilized streptavidin, glutathione and nickel chelator plates.

SUMMARY

What is needed are methods and devices with lower interference, improved ruggedness, resilience to strong wash conditions, finely tuned binding capacities, and reduced non-specific binding that can be used in the preparation of samples that are to be assayed by LC-MS. Adsorption-based immunocapture and enzymatic sample preparation devices are compromised by the contamination they can exhibit from desorbed ligands and blocking agents, such as polyethylene glycol sorbitan monolaurate. The methods and devices of the present technology provide a material that is easily tuned to have minimal, undesired, secondary interactions with an analyte of interest.

One benefit of the technology is that the methods and devices are very robust due to the chemical attachment (covalent bond) between an affinity ligand or enzyme and the underlying alkylsilyl coating. This allows for the regeneration and re-use of the devices as well as prevents interference or bleed of the biological ligand into the purified analyte. In addition, the devices are highly tunable due to the silane nature of the bonds. A micro-environment can be adjusted to ensure the stabilization of the affinity ligand or enzyme.

The present technology relates to a coated device used for LC-MS sample preparation that is based on an alkylsilyl composition and covalently immobilized biological ligands. It provides a ready-to-use device for anti-human Fc domain capture, wherein there is no dependence on a non-covalent interaction other than the one corresponding to the ligand:

target human Fc domain complex. In addition, a secondary resin layer can be used to afford increased surface area and binding capacity.

In one aspect, the technology features a sample preparation device for enriching a component of a sample. The sample preparation device includes a surface in fluid communication with the sample, an alykylsilyl coating disposed on the surface, and an affinity ligand or an enzyme covalently bonded to the alkylsilyl coating. The sample preparation device can include one or more of the embodiments described herein.

In some embodiments, an affinity ligand is bonded to the alkylsilyl coating. More than one affinity ligand can be bonded to the alkylsilyl coating. In other embodiments, an enzyme is bonded to the alkylsilyl coating. More than one enzyme can be bonded to the alkylsilyl coating.

In some embodiments, the alkylsilyl coating has a thickness of at least 100 Å.

The surface can be an interior surface of a well plate, an interior surface of a vial, or an interior surface of a pipette.

In some embodiments, the sample preparation device is used for chromatographic analysis. The sample preparation device can be used for mass spectrometric analysis.

In some embodiments, the alkylsilyl is an inert coating, e.g., the alkylsilyl coating does not interact with an analyte in a sample. The alkylsilyl coating can have the Formula I:

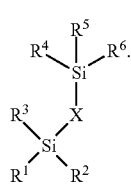

(I)

$R^1$, $R^2$, $R^3$, $R^4$, $R^5$, and $R^6$ are each independently selected from $(C_1-C_6)$alkoxy, —$NH(C_1-C_6)$alkyl, —$N((C_1-C_6)$alkyl$)_2$, OH, $OR^A$, and halo. $R^A$ represents a point of attachment to the surface. At least one of $R^1$, $R^2$, $R^3$, $R^4$, $R^5$, and $R^6$ is $OR^A$. X is $(C_1-C_{20})$alkyl, —$O[(CH_2)_{1-20}]$—, —$(C_1-C_{10})[NH(CO)NH(C_1-C_{10})]_{1-20}$-, or —$(C_1-C_{10})[$alkylphenyl$(C_1-C_{10})$alkyl$]_{1-20}$-.

In some embodiments X is $(C_2-C_{10})$alkyl. In some embodiments, X is ethyl. $R^1$, $R^2$, $R^3$, $R^4$, $R^5$, and $R^6$ can each be methoxy or chloro. In some embodiments, the alkylsilyl coating of Formula I is bis(trichlorosilyl)ethane or bis(t-rimethoxysilyl)ethane.

The sample preparation device can also include a second alkylsilyl coating in direct contact with the alkylsilyl coating of Formula I. The second alkylsilyl coating can have the Formula II:

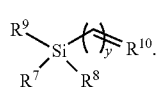

(II)

$R^7$, $R^8$, and $R^9$ are each independently selected from —NH$(C_1-C_6)$alkyl, —N$[(C_1-C_6)$alkyl$]_2$, $(C_1-C_6)$alkoxy, $(C_1-C_6)$alkyl, $(C_1-C_6)$alkenyl, OH, and halo. $R^{10}$ is selected from $(C_1-C_6)$alkyl, —$OR^B$, —$[O(C_1-C_3)$alkyl$]_{1-10}O(C_1-C_6)$alkyl, and phenyl, wherein said $(C_1-C_6)$alkyl is optionally substituted with one or more halo and wherein said phenyl is optionally substituted with one or more groups selected from $(C_1-C_3)$alkyl, hydroxyl, fluorine, chlorine, bromine, cyano, —$C(O)NH_2$, and carboxyl. $R^B$ is —$(C_1-C_3)$alkyloxirane, —$(C_1-C_3)$alkyl-3,4-epoxycyclohexyl, or —$(C_1-C_4)$alkylOH. The hashed bond to $R^{10}$ represents an optional additional covalent bond between $R^{10}$ and the carbon bridging the silyl group to form an alkene, provided y is not 0. y is an integer from 0 to 20. The second alkylsilyl coating can modify the alkylsilyl coating of Formula I.

In some embodiments, y is an integer from 2 to 9. In some embodiments, y is 9, $R^{10}$ is methyl, and $R^7$, $R^8$, and $R^9$ are each ethoxy or chloro.

In some embodiments, the alkylsilyl coating of Formula II is (3-glycidyloxypropyl)trimethoxysilane, n-decyltrichlorosilane, trimethylchlorosilane, trimethyldimethyaminosilane, or methoxy-polyethyleneoxy(1-10)silane. In some embodiments, the alkylsilyl coating of Formula II is (3-glycidyloxypropyl)trimethoxysilane followed by hydrolysis. The alkylsilyl coating of Formula I can be bis(trichlorosilyl)ethane or bis(trimethoxysilyl)ethane and the alkylsilyl coating of Formula II can be (3-glycidyloxypropyl)trimethoxysilane. In some embodiments, the alkylsilyl coating of Formula I is bis(trichlorosilyl)ethane or bis(trimethoxysilyl)ethane and the alkylsilyl coating of Formula II is (3-glycidyloxypropyl)trimethoxysilane followed by hydrolysis. The alkylsilyl coating of Formula I can be bis(trichlorosilyl)ethane or bis(trimethoxysilyl)ethane and the alkylsilyl coating of Formula II can be n-decyltrichlorosilane. In some embodiments, the alkylsilyl coating of Formula I is bis(trichlorosilyl)ethane or bis(trimethoxysilyl)ethane and the alkylsilyl coating of Formula II is trimethylchlorosilane or trimethyldimethyaminosilane. The alkylsilyl coating of Formula I can be bis(trichlorosilyl)ethane or bis(trimethoxysilyl)ethane and the alkylsilyl coating of Formula II can be methoxy-polyethyleneoxy(3)silane.

In some embodiments, the sample preparation device also includes a alkylsilyl coating having the Formula III in direct contact with the alkylsilyl coating of Formula I,

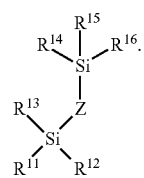

(III)

$R^{11}$, $R^{12}$, $R^{13}$, $R^{14}$, $R^{15}$, and $R^{16}$ are each independently selected from $(C_1-C_6)$alkoxy, —$NH(C_1-C_6)$alkyl, —$N((C_1-C_6)$alkyl$)_2$, OH, and halo. Z is $(C_1-C_{20})$alkyl, —O$[(CH_2)_2O]_{1-20}$—, —$(C_1-C_{10})[NH(CO)NH(C_1-C_{10})]_{1-20}$-, or —$(C_1-C_{10})[$alkylphenyl$(C_1-C_{10})$alkyl$]_{1-20}$-. The alkylsilyl coating of Formula III can modify the alkylsilyl coating of Formula I.

In some embodiments, the alkylsilyl coating of Formula III is bis(trichlorosilyl)ethane or bis(trimethoxysilyl)ethane. The alkylsilyl coating of Formula I can be bis(trichlorosilyl)ethane or bis(trimethoxysilyl)ethane and the alkylsilyl coating of Formula III can be bis(trichlorosilyl)ethane or bis(trimethoxysilyl)ethane.

In some embodiments, the alkylsilyl coating of I and III has a total thickness of about 400 Å.

In some embodiments, the alkylsilyl coating is an active coating, e.g., the alkylsilyl coating reacts with an analyte in a sample. The alkylsilyl coating can be selected to interact with at least one analyte in the sample through (1) a repulsive force, (2) a secondary interaction, or (3) a retention mechanism distinct from the interaction with a stationary phase material.

In some embodiments, the analyte and the active coating are negatively charged. The analyte and active coating can be positively charged. In some embodiments, the secondary interaction is ion exchange partitioning.

In some embodiments, the alkyl silyl coating has the Formula IV:

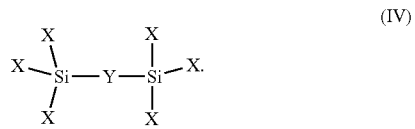

(IV)

Each X is independently selected from $(C_1-C_6)$alkoxy, —NH$(C_1-C_6)$alkyl, —N$((C_1-C_6)$alkyl$)_2$, OH, OR$^A$, R$^B$, R$^C$, R$^D$ and halo. R$^A$ represents a point of attachment to the surface of the sample preparation device or a frit and at least one X is OR$^A$. R$^B$ is absent or represents a hydrophobicity modifier. R$^C$ represents a charge modifier and at least one X is R$^C$. R$^D$ is absent, a chelator, or a crown ether. Y is a bridging moiety selected from $(C_1-C_{20})$alkyl, —O[(CH$_2$)$_2$O]$_{1-20}$—, —$(C_1-C_{10})$[NH(CO)NH$(C_1-C_{10})$]$_{1-20}$-, or —$(C_1-C_{10})$[alkylphenyl$(C_1-C_{10})$alkyl]$_{1-20}$-.

In some embodiments, the charge modifier (R$^C$) is

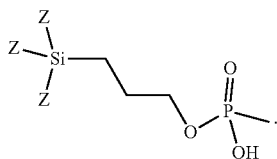

Z is independently selected from $(C_1-C_6)$alkoxy, —NH$(C_1-C_6)$alkyl, —N$((C_1-C_6)$alkyl$)_2$, OH, halo, or an attachment point to Formula IV. At least one Z is the attachment point to Formula IV.

In some embodiments, the charge modifier (R$^C$) is

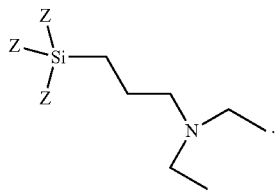

Z is independently selected from $(C_1-C_6)$alkoxy, —NH$(C_1-C_6)$alkyl, —N$((C_1-C_6)$alkyl$)_2$, OH, halo, or an attachment point to Formula I. At least one Z is the attachment point to Formula IV.

In some embodiments, the charge modifier (R$^C$) is a quaternary amine.

In some embodiments, the hydrophobicity modifier (R$^B$) is present. The hydrophobicity modifier (R$^B$) can have a net neutral charge. In some embodiments, the hydrophobicity modifier (R$^B$) is

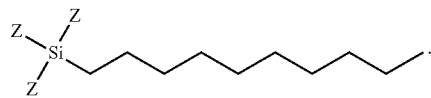

Z is independently selected from $(C_1-C_6)$alkoxy, —NH$(C_1-C_6)$alkyl, —N$((C_1-C_6)$alkyl$)_2$, OH, halo, or an attachment point to Formula IV. At least one Z is the attachment point to Formula IV.

In some embodiments, the hydrophobicity modifier (R$^B$) is

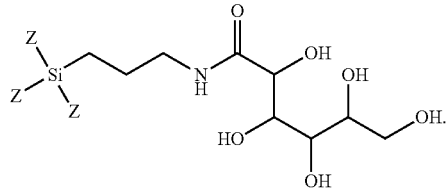

Z is independently selected from $(C_1-C_6)$alkoxy, —NH$(C_1-C_6)$alkyl, —N$((C_1-C_6)$alkyl$)_2$, OH, halo, or an attachment point to Formula IV. At least one Z is the attachment point to Formula IV.

In some embodiments, R$^D$ is present. R$^D$ can be the chelator and the chelator is ethylenediaminetetraacetic acid. In some embodiments, R$^D$ is the chelator and the chelator is etidronic acid. R$^D$ can be the crown ether and the crown ether is selected from the group consisting of 18-crown-6, 12-crown-4, 15-crown-5, dibenzo-18-crown-6, and diaza-18-crown-6.

The affinity ligand can be an antibody, a single domain antibody, an aptamer, an affimer, streptavidin, protein A, protein G, or protein L, or a combination thereof.

In some embodiments, the sample preparation device also includes a linker (or a spacer molecule) to covalently bond the affinity ligand or enzyme to the alkylsilyl coating. The linker can be a maleimide PEG silane, an NHS PEG Maleimide, or PEG dialdehyde, where the PEG repeat is between 3 and 300. In some embodiments, the linker is glutaraldehyde or acryloxysilane.

In some embodiments, the covalent bond between the affinity ligand or enzyme and the alkylsilyl coating is made through reductive amination.

The affinity ligand can have a surface coverage of about 1 to about 1000 nmol/m$^2$. In some embodiments, the affinity ligand has a surface coverage of about 2 to about 500 nmol/m$^2$.

In some embodiments, the enzyme is selected from proteases, glycosidases, ligases, transferases, oxidoreductases, isomerases, hydrolases, or a combination thereof. The enzyme can be a protease and the protease can be selected from IdeS, IdeZ, or a combination thereof. In some embodiments, the enzyme is β-glucuronidase. The enzyme can have a surface coverage of about 1 to about 1000 nmol/m$^2$. In some embodiments, the enzyme has a surface coverage of about 2 to about 500 nmol/m$^2$.

In some embodiments, the affinity ligand has the sequence depicted in SEQ ID NO: 1. The affinity ligand can be at least 75%, 80%, 85%, 90%, 95%, 98%, or 99% identical to the sequence depicted in SEQ ID NO: 1.

In some embodiments, the affinity ligand has the sequence depicted in SEQ ID. NO: 2. The affinity ligand can be at least 75%, 80%, 85%, 90%, 95%, 98%, or 99% identical to the sequence depicted in SEQ ID NO: 2.

In some embodiments, the enzyme has the sequence depicted in SEQ ID. NO: 3. The enzyme can be at least 75%, 80%, 85%, 90%, 95%, 98%, or 99% identical to the sequence depicted in SEQ ID NO: 3.

In some embodiments, the enzyme has the sequence depicted in SEQ ID. NO: 4. The enzyme can be at least 75%, 80%, 85%, 90%, 95%, 98%, or 99% identical to the sequence depicted in SEQ ID NO: 4.

In another aspect, the technology features a sample preparation device for enriching a component of a sample. The sample preparation device includes a surface in fluid communication with the sample, an alkylsilyl coating disposed on the surface, a resin made of silica, organosilica or a polymer, the resin covalently bonded to the alkylsilyl coating, and an affinity ligand or an enzyme covalently bonded to the resin. The sample preparation device can include one or more of the embodiments described herein.

In some embodiments, the resin is covalently bonded to the alkylsilyl coating by a silane.

The sample preparation device can be used for chromatographic analysis, mass spectrometric analysis or a combination thereof.

In another aspect, the technology features a method of analyzing a biofluid. The method includes providing a sample preparation device. The sample preparation device includes a surface in fluid communication with the biofluid, an alkylsilyl coating disposed on the surface, and an affinity ligand covalently bonded to the alkylsilyl coating. The method also includes aspirating the biofluid comprising an analyte onto the surface of the sample preparation device to form an affinity complex such that the analyte is adsorbed. The adsorbed analyte is washed with a neutral, isotonic buffer. The adsorbed analyte is eluted from from the surface of the sample preparation device. The method also includes analyzing the eluted sample using liquid chromatography, mass spectrometry, ELISA, capillary electrophoresis, or a combination thereof. The method can include one or more of the embodiments described herein.

In some embodiments, the sample preparation device is a 96 well microelution plate, a tapered bottom vial or a pipette tip.

The affinity ligand can be capable of capturing human immoglobulin Fc domains. In some embodiments, the affinity ligand is a nucleic acid aptamer, an immunoglobulin, a single domain VHH camelid antibody, or a combination thereof.

In another aspect, the technology features a method of separating a biofluid. The method includes providing a frit. The frit includes a surface in fluid communication with the biofluid, an alkylsilyl coating disposed on the surface, and an affinity ligand covalently bonded to the alkylsilyl coating. The frit is positioned at the inlet of a chromatography column. The method also includes loading the biofluid comprising an analyte onto the surface of the frit, capturing the analyte to form an affinity complex such that the analyte is adsorbed on the surface of the frit while a remainder of the biofluid passes through the chromatography column, eluting the adsorbed analyte from the surface of the frit such that the analyte passes through the chromatography column, and detecting the analyte with a detector. The method can include one or more of the embodiments described herein.

In some embodiments, the chromatography column is a size exclusion chromatography column. The detector can be a mass spectrometer.

In some embodiments, the biofluid comprises a humanized mAb based therapeutic.

The affinity ligand can be an anti-human Fc aptamer, an anti-human Fc immunoglobulin antibody, an anti-human Fc single domain antibody ligand, or a combination thereof.

In another aspect, the technology features a method for quantifying opioid glucuronides. The method includes providing a sample preparation device. The sample preparation device includes a surface in fluid communication with a sample comprising the opioid glucuronides, an alkylsilyl coating disposed on the surface, and a β-glucuronidase enzyme covalently bonded to the alkylsilyl coating. The method also includes aspirating the sample comprising the opioid glucuronides onto the surface of the sample preparation device such that the opioid glucuronides is hydrolyzed. The hydrolyzed opioid glucuronides is recovered from the surface of the sample preparation device. The recovered hydrolyzed opioid glucuronides is injected onto a liquid chromatography column. The method can include one or more of the embodiments described herein.

In another aspect, the technology features a method of preparing a sample comprising a protein for peptide mapping. The method includes providing a sample preparation device. The sample preparation device includes a surface in fluid communication with the sample comprising the protein, an alkylsilyl coating disposed on the surface, and a protease enzyme covalently bonded to the alkylsilyl coating, wherein the protease enzyme is trypsin, Lys-C, Arg-C, Lys-N, Glu-C, Asp-N, pepsin, or a combination thereof. The method also includes aspirating the sample comprising the protein onto the surface of the sample preparation device such that the protein is digested into peptide fragments. The peptide fragments are recovered from the sample preparation device and the peptide fragments are injected onto a liquid chromatography column. The method can include one or more of the embodiments described herein.

In some embodiments, the protease enzyme is trypsin, Lys-C, Asp-N, or a combination thereof.

The alkylsilyl coating can be bis(trichlorosilyl)ethane and the protease enzyme can be trypsin, wherein the trypsin is covalently bonded to the bis(trichlorosilyl)ethane by a maleimide PEG silane linker. In some embodiments, the maleimide PEG silane linker is:

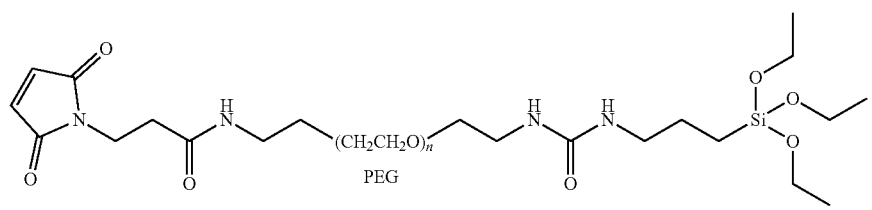

wherein n is between 3 and 300.

In some embodiments, the alkylsilyl coating is bis(trichlorosilyl)ethane modified with triethoxysilyl butyraldehyde and the protease enzyme is trypsin, wherein the trypsin is covalently bonded to the triethoxysilyl butyraldehyde modified bis(trichlorosilyl)ethane by reductive amination. The alkylsilyl coating can be bis(trichlorosilyl)ethane modified with 3-aminopropyl trimethoxysilane and the protease enzyme can be trypsin, wherein the trypsin is covalently bonded to the 3-aminopropyl trimethoxysilane modified bis(trichlorosilyl)ethane by reductive amination with a PEG dialdehyde. In some embodiments, the PEG dialdehyde is:

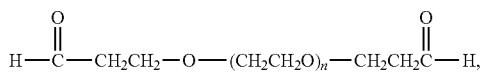

wherein n is between 3 and 300.

In some embodiments, the the alkylsilyl coating is bis (trichlorosilyl)ethane modified with triethoxysilyl butyraldehyde and acrylate PEG amine, and the protease enzyme is trypsin, wherein the trypsin is covalently bonded to the modified bis(trichlorosilyl)ethane by reductive amination and Michael addition. The acrylate PEG amine can be:

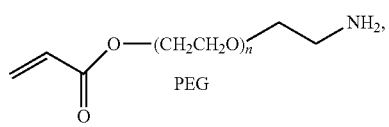

wherein n is between 3 and 300.

In some embodiments, the alkylsilyl coating is bis(trichlorosilyl)ethane modified with acryloxypropyltrimethoxy silane and the protease enzyme is trypsin, wherein the trypsin is covalently bonded to the acryloxypropyltrimethoxy silane modified bis(trichlorosilyl)ethane by Michael addition.

In another aspect, the technology features a method of analyzing a sample comprising monoclonal antibodies (mAb). The method includes providing a sample preparation device. The sample preparation device includes a surface in fluid communication with the sample comprising the mAb, an alkylsilyl coating disposed on the surface, and an enzyme covalently bonded to the alkylsilyl coating, wherein the enzyme is IdeS, IdeZ, IgdE, Gingipain K or a combination thereof. The method also includes aspirating the sample comprising the mAb onto the surface of the sample preparation device such that the mAb is fragmented into subunits. The subunits of the mAb are recovered from the sample preparation device and the subunits of the mAb are injected onto a liquid chromatography column. The method can include one or more of the embodiments described herein.

In another aspect, the technology features a method of analyzing a sample comprising a glycoprotein. The method includes providing a sample preparation device. The sample preparation device includes a surface in fluid communication with the sample comprising the glycoprotein, an alkylsilyl coating disposed on the surface, and a PNGase F enzyme covalently bonded to the alkylsilyl coating. The method also includes aspirating the sample comprising the glycoprotein onto the surface of the sample preparation device such that the glycans of the glycoprotein are cleaved. The deglycosylated glycoprotein is recovered from the sample preparation device and the deglycosylated glycoprotein is injected onto a liquid chromatography column. The method can include one or more of the embodiments described herein.

BRIEF DESCRIPTION OF THE FIGURES

FIG. 4 is a chart showing exemplary embodiments of active coatings, in accordance with an illustrative embodiment of the technology.

FIG. 5A is a table summarizing several examples of coatings and immobilized biological ligands, in accordance with an illustrative embodiment of the technology.

FIG. 5B is a continuation of the table of FIG. 5A, showing additional columns relating to Formula II and Formula III, in accordance with an illustrative embodiment of the technology.

FIG. 5C is a continuation of the table of FIGS. 5A and 5B, showing additional columns relating to Linkage and Biological Ligands, in accordance with an illustrative embodiment of the technology.

DETAILED DESCRIPTION

The technology includes devices, compositions, and methods of using devices and LC flow path components (e.g., frits) that are modified with an organosilica (alkylsilyl) functionality and derivatized to bear immobilized affinity ligands and/or enzymes. With this technology, surfaces are created that are advantageous for use in various types of off-line and online liquid chromatography-mass spectrometry (LC-MS) sample preparations, ranging from the quantitation of monoclonal antibodies (mAb) in biofluids to the use of a β-glucuronidase enzyme device for assisting in the quantitation of opioid glucuronides. In one exemplary embodiment, a surface is vapor deposition coated with an alkyl silyl coating and subsequently treated using a liquid phase reaction that results in the immobilization of an affinity ligand with capture selectivity for human immunoglobulin Fc domains.

Devices

Figure 1:
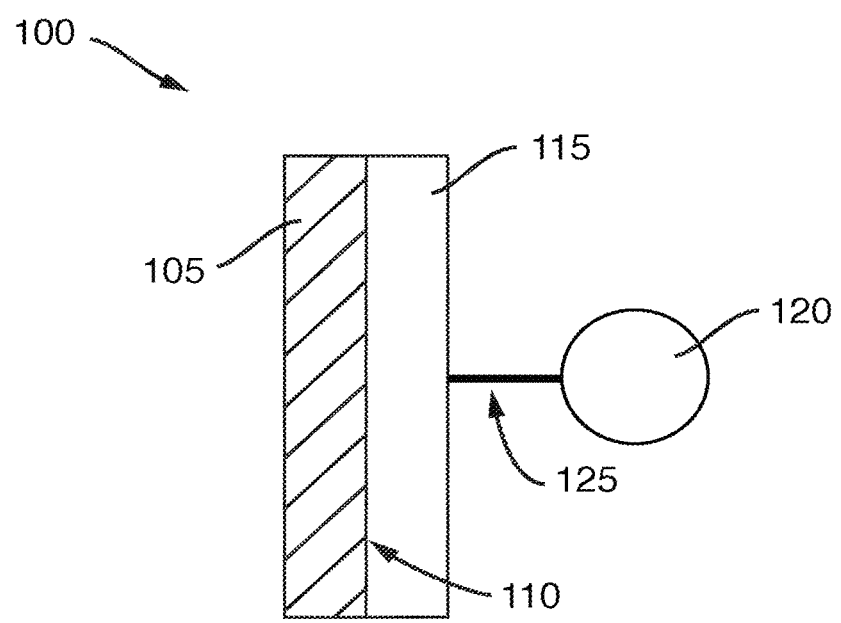
FIG. 1 is a schematic representation of a sample preparation device for enriching a component of a sample, according to an illustrative embodiment of the technology.

FIG. 1 is a schematic representation of a sample preparation device 100 for enriching a component of a sample. The device 100 includes a substrate 105 that has a surface 110. The surface is in fluid communication with the sample. The substrate 105 can be, for example, a well plate, a vial, a pipette or any other substrate used in sample preparation. The surface 110, can be an interior surface (e.g., a surface that is in fluid communication with the sample), of a well plate (also called a microelution plate), an interior surface of a vial (e.g., a tapered bottom vial) or an interior surface of a pipette (e.g., a pipette tip). The surface 110 can be any surface that is in fluid communication with, or comes into contact with, the sample, for example, a frit at an inlet of a chromatography column. An alkylsilyl (organosilica) coating 115 is disposed on the surface 110. The alkylsilyl coating 115 can be disposed on the surface 110 through a variety of means, for example, the alkylsilyl coating 115 can be vapor deposited on the surface 110. A biological ligand 120, for example an affinity ligand and/or an enzyme can be covalently bonded 125 to the alkylsilyl coating 115. The sample preparation device 100 can be used for chromatographic analysis and/or mass spectrometric analysis.

Figure 2:
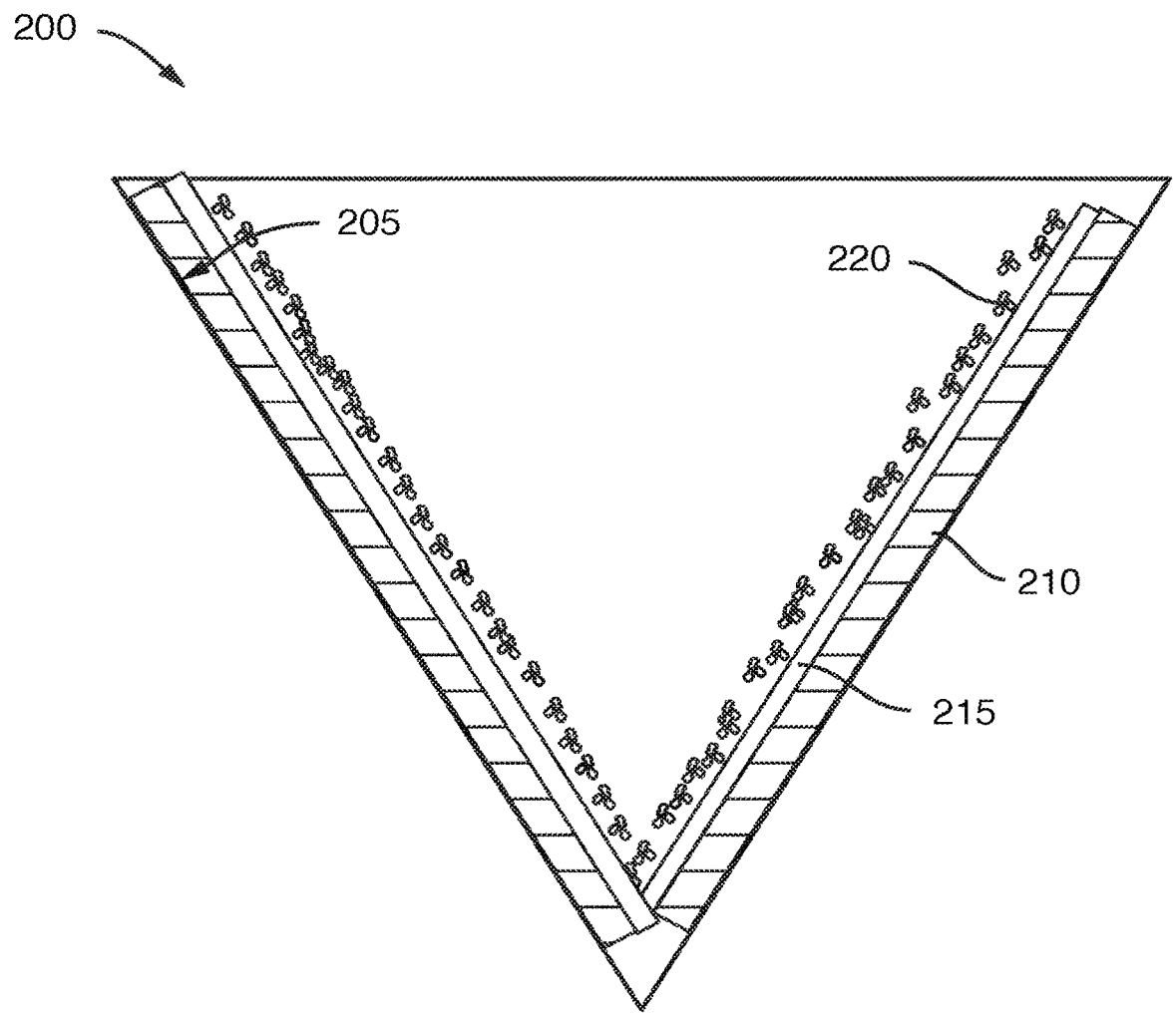
FIG. 2 is a schematic representation of a microvolume well for enriching a component of a sample, according to an illustrative embodiment of the technology.

FIG. 2 is a schematic representation of a microvolume well 200 for enriching a component of a sample. The microvolume well 200 can be a part of a well plate, for example, a 96-well plate. As discussed above, the microvolume well 200 has a surface 205 (e.g., an interior surface) that is in fluid communication with the sample. An alkylsilyl coating 210 is disposed on the surface 205. In some embodiments, there is an optional surface modifying coating 215 that is deposited onto the alkylsilyl coating 210. The optional surface modifying coating 215 can be, for example, a second alkylsilyl coating, a charge modifier, a hydrophobicity modifier, a chelator and/or a crown ether. A biological ligand 220, for example an affinity ligand and/or an enzyme, can be covalently bonded to either the alkylsilyl coating 210 or the optional surface modifying coating 215. The microvolume well 200 can be used for chromatographic analysis and/or mass spectrometric analysis.

Figure 3:
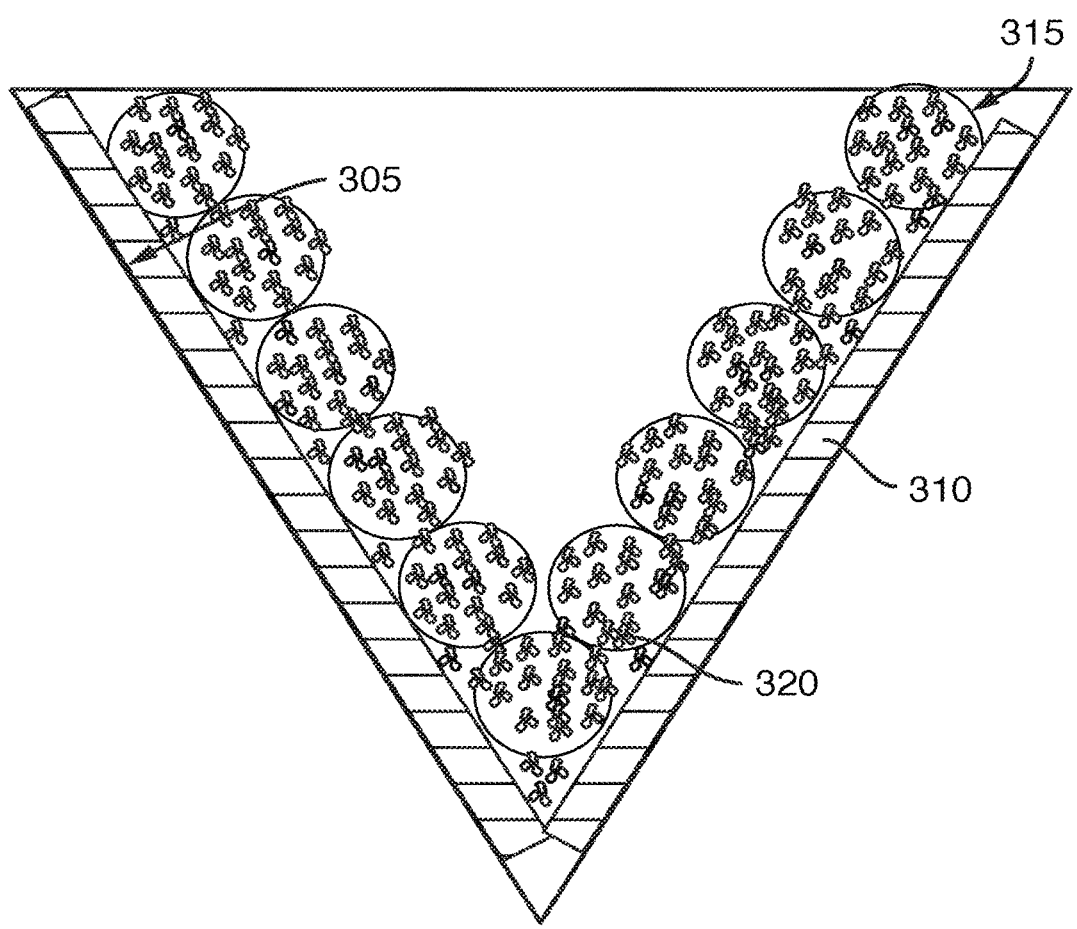
FIG. 3 is a schematic representation of a microvolume well that has been derivatized to have a coated surface with immobilized biological ligands and a secondary layer of resin, according to an illustrative embodiment of the technology.

FIG. 3 is a schematic representation of a microvolume well 300 that has been derivatized to have a coated surface with immobilized biological ligands and a secondary layer of resin. The microvolume well 300 can be a part of a well plate, for example, a 96-well plate. As discussed above, the microvolume well 300 has a surface 305 (e.g., an interior surface) that is in fluid communication with the sample. An alkylsilyl coating 310 is disposed on the surface 305. In some embodiments, there is an optional surface modifying coating (not shown). A resin 315, made of silica, organosilica, or a polymer is covalently bonded to the alkylsilyl coating 310 (or the optional surface modifying coating). The resin 315 can be covalently bonded to the alkylsilyl coating 310 by a silane. A biological ligand 320, e.g., an affinity ligand and/or an enzyme, is covalently bonded to the resin 315. The microvolume well 300 can be used for chromatographic analysis and/or mass spectrometric analysis.

The resin 315 can be derived from either spherical or non-spherical irregular particles made of silica, organosilica, or polymer. The resin 315 can form a layer over of the alyklsilyl coating 310. The resin 315 increases the surface area in which the biological ligand 320 can be bonded and therefore increases the capacity of the sample preparation device, a microvolumne well 300 in FIG. 3. Non-porous resin can be used for applications that are sensitive to diffusion effects. Porous resin can be used where it is more critical to have high surface area as the pores of the resin increase the total surface area.

Alkylsilyl Coatings

Organosilica (alkylsilyl) is a versatile composition to use in the coating of both metallic and polymeric flow path components, which can range from sample preparation devices, an injector needle and pre-column heater to post-column tubing, column housings, frits, detector flow cells, and electrospray needles. The organosilica (alkyksilyl) coating can be applied via either gas phase or solution phase reactions and with a host of different silanizing reagents. For example, an alkylsilyl coating can be applied via vapor deposition.

In one embodiment, it is advantageous to first apply a bis-silyl or tris-silyl bridging silane reagent via vapor deposition to achieve a high build, >100 Å thick base layer (e.g., Formula I as described herein), as can be achieved using previously described techniques (e.g., those described in U.S. patent application Ser. No. 16/133,089, filed on Sep. 17, 2018, and published on Mar. 21, 2019 as US patent publication no. 2019-0086371, the entire contents of which is incorporated herein by reference). One exemplary silane of proven utility for forming this base layer is bis(trichlorosilyl)ethane. Optionally, this base layer can be modified with charge modifying or hydrophobicity/hydrophilicity modifying silanizing reagents (including but not limited to the reagents described herein for charge modifiers ($R^C$) and hydrophobicity modifiers ($R^B$)). These surface modifiers can be comprised of strong acids/bases or weak acids/bases with a dissociation constant selected in a desirable range of pKa and can include but are not limited to trimethoxy silyl propyl methyl phosphonate and N,N-(diethylaminopropyl) trimethoxysilane. Surface modifiers with fixed charges, such as quaternary amines, can also be employed. Alternatively, primary and secondary amine containing silanes can be used, which also afford nucleophiles for subsequent immobilization reactions. Moreover, an aldehyde containing silane, such as triethoxysilyl butyraldehyde, can be used to afford a site for reductive amination linkage or an acryloxypropyltrimethoxysilane for Michael addition. These surface modifiers can be incorporated in situ during a vapor deposition process or through secondary, liquid phase reactions. In some instances, it may be necessary for these liquid phase reactions to include multiple steps so as to build a desired thickness and/or coverage of the modifying silane. The surface to be modified with a charge modifier can have a coverage of about 0.01 to about 10 µmol/m², about 0.02 to about 1 µmol/m². In another embodiment, the bridging silane base layer can alternatively be derivatized with a net neutral charge hydrophobicity modifier ($R^B$ described herein). In other embodiments, they are not. Encompassed within these reagent choices are zwitterionic modifiers, such as carboxy- and sulfobetaine reagents. A zwitterionic modifier can afford a macroscopically, net neutral surface, but it can also lend microscopic Coulombic effects that can be anti-bind or repulsive for a wide range of analytes, including those with diverse charge characteristics. As with a charge bearing surface modifier, a hydrophobicity modifier can be deposited with surface coverages ranging from 0.01 to 10 µmol/m².

The term "about" denotes that the thereafter following value is not an exact value but is the center point of a range that is +/−5% of the value. If the value is a relative value given in percentages the term "about" also denotes that the thereafter following value is not an exact value but is the center point of a range that is +/−5% of the value, whereby the upper limit of the range cannot exceed a value of 100%.

Exemplary alkylsilyl coatings that can be used include bio-inert coatings, for example, those described in U.S. patent application Ser. No. 16/133,089, filed on Sep. 17, 2018, and published on Mar. 21, 2019 as US patent publication no. 2019-0086371, the entire contents of which is incorporated herein by reference. In addition, active coatings (coatings that interact with the analyte or mobile phase) can also be used.

Inert Coatings

In some aspects, the alkylsilyl coating is used to modify a sample preparation device or a flow path of a chromatography system to address interactions with, for example, an analyte. That is, the alkylsilyl coating can be a bioinert, low-bind coating, which minimizes surface reactions with the metal interacting analyte and allows the analyte to pass along a flow path without clogging, attaching to surfaces, or change in analyte properties. The reduction/elimination of these interactions is advantageous because it allows for accurate quantification and analysis of a sample containing a metal-interacting analyte, for example biomolecules, proteins, glycans, peptides, oligonucleotides, pesticides, bisphosphonic acids, anionic metabolites, and zwitterions like amino acids and neurotransmitters. The alkylsilyl coating can have the Formula I:

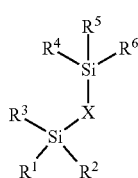

(I)

$R^1$, $R^2$, $R^3$, $R^4$, $R^5$, and $R^6$ are each independently selected from $(C_1-C_6)$alkoxy, —NH$(C_1-C_6)$alkyl, —N$((C_1-C_6)$alkyl$)_2$, OH, OR$^A$, and halo. R$^A$ represents a point of attachment to the interior surfaces of the sample preparation device, e.g., interior surface 110 of FIG. 1 or to a surface of a frit. At least one of $R^1$, $R^2$, $R^3$, $R^4$, $R^5$, and $R^6$ is OR$^A$. X is $(C_1-C_{20})$alkyl, —O[(CH$_2$)$_2$O]$_{1-20}$—, —$(C_1-C_{10})$[NH(CO)NH$(C_1-C_{10})$]$_{1-20}$-, or —$(C_1-C_{10})$[alkylphenyl$(C_1-C_{10})$alkyl]$_{1-20}$-.

In some embodiments, X is $(C_2-C_{10})$alkyl. X can be ethyl. In some embodiments, $R^1$, $R^2$, $R^3$, $R^4$, $R^5$, and $R^6$ are each methoxy or chloro. The alkylsilyl coating of Formula I can be bis(trichlorosilyl)ethane or bis(trimethoxysilyl)ethane.

In some embodiments, the assembly also includes a second alkylsilyl coating in direct contact with the alkylsilyl coating of Formula I. The second alkylsilyl coating has the Formula II:

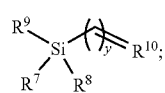

(II)

$R^7$, $R^8$, and $R^9$ are each independently selected from —NH$(C_1-C_6)$alkyl, —N[$(C_1-C_6)$alkyl]2, $(C_1-C_6)$alkoxy, $(C_1-C_6)$alkyl, $(C_1-C_6)$alkenyl, OH, and halo. $R^{10}$ is selected from $(C_1-C_6)$alkyl, —OR$^B$, —[O$(C_1-C_3)$alkyl]$_{1-10}$O$(C_1-C_6)$alkyl, and phenyl. The $(C_1-C_6)$alkyl is optionally substituted with one or more halo. The phenyl is optionally substituted with one or more groups selected from $(C_1-C_3)$alkyl, hydroxyl, fluorine, chlorine, bromine, cyano, —C(O)NH$_2$, and carboxyl. R$^B$ is —$(C_1-C_3)$alkyloxirane, —$(C_1-C_3)$alkyl-3,4-epoxycyclohexyl, or —$(C_1-C_4)$alkylOH. The hashed bond to $R^{10}$ represents an optional additional covalent bond between $R^{10}$ and the carbon bridging the silyl group to form an alkene, provided y is not 0. y is an integer from 0 to 20.

In some embodiments, y is an integer from 2 to 9. In some embodiments, y is 9, $R^{10}$ is methyl, and $R^7$, $R^8$, and $R^9$ are each methoxy, ethoxy or chloro. The alkylsilyl coating of Formula II can be (3-glycidyloxypropyl)trimethoxysilane, n-decyltrichlorosilane, trimethylchlorosilane, trimethyldimethyaminosilane, or methoxy-polyethyleneoxy(1-10)silane. In some embodiments, the alkylsilyl coating of Formula II is (3-glycidyloxypropyl)trimethoxysilane followed by hydrolysis.

The alkylsilyl coating of Formula I can be bis(trichlorosilyl)ethane or bis(trimethoxysilyl)ethane and the alkylsilyl coating of Formula II can be (3-glycidyloxypropyl)trimethoxysilane. In some embodiments, the alkylsilyl coating of Formula I is bis(trichlorosilyl)ethane or bis(trimethoxysilyl)ethane and the alkylsilyl coating of Formula II is (3-glycidyloxypropyl)trimethoxysilane followed by hydrolysis. The alkylsilyl coating of Formula I can be bis(trichlorosilyl)ethane or bis(trimethoxysilyl)ethane and the alkylsilyl coating of Formula II can be n-decyltrichlorosilane. In some embodiments, the alkylsilyl coating of Formula I is bis(trichlorosilyl)ethane or bis(trimethoxysilyl)ethane and the alkylsilyl coating of Formula II is trimethylchlorosilane or trimethyldimethyaminosilane. The alkylsilyl coating of Formula I can be bis(trichlorosilyl)ethane or bis(trimethoxysilyl)ethane and the alkylsilyl coating of Formula II can be methoxy-polyethyleneoxy(3)silane.

In some embodiments, the assembly also includes an alkylsilyl coating having the Formula III in direct contact with the alkylsilyl coating of Formula I. The alkylsilyl coating of Formula III is:

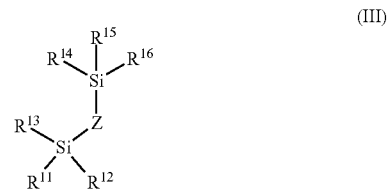

(III)

$R^{11}$, $R^{12}$, $R^{13}$, $R^{14}$, $R^{15}$, and $R^{16}$ are each independently selected from $(C_1-C_6)$alkoxy, —NH$(C_1-C_6)$alkyl, —N$((C_1-C_6)$alkyl$)_2$, OH, and halo. Z is $(C_1-C_{20})$alkyl, —O[(CH$_2$)$_2$O]$_{1-20}$—, —$(C_1-C_{10})$[NH(CO)NH$(C_1-C_{10})$]$_{1-20}$-, or —$(C_1-C_{10})$[alkylphenyl$(C_1-C_{10})$alkyl]$_{1-20}$-.

In some embodiments, the alkylsilyl coating of Formula III is bis(trichlorosilyl)ethane or bis(trimethoxysilyl)ethane. The alkylsilyl coating of Formula I can be bis(trichlorosilyl)ethane or bis(trimethoxysilyl)ethane and the alkylsilyl coating of Formula III can be bis(trichlorosilyl)ethane or bis(trimethoxysilyl)ethane.

In the present technology, vapor deposited alkylsilyl coatings on surfaces of sample preparation devices or frits modify the surface and decrease secondary interactions. As such, they are bioinert or low-bind (meaning that analytes of a sample do not interact with the alkylsilyl coating). In addition, the deposited coatings are highly tunable to provide a range of desirable contact angles (e.g., make the wetted surfaces hydrophilic or hydrophobic), chemistries, and properties to achieve a desired effect on the flow path and ultimately the sample passing through the flow path.

The thickness of the alkylsilyl coating can be at least about 100 Å. For example the thickness can be between about 100 Å to about 1600 Å. The thickness of the multilayered alkylsilyl coating for Formal I can be about 100 Å, 200 Å, 300 Å, 400 Å, 500 Å, 600 Å, 700 Å, 800 Å, 900 Å, 1000 Å, 1100 Å, 1200 Å, 1300 Å, 1400 Å, 1500 Å or 1600 Å.

Exemplary coatings with their respective approximate thickness and contact angle are provided in Table 1.

TABLE 1

| VPD# | Vapor Deposited Material | Alternative Coating Abbreviation | Approximate Thickness of Product | Approximate Contact Angle |
|---|---|---|---|---|
| 1 | bis(trichlorosilyl)ethane or bis(trismethoxysilyl)ethane as a first layer followed by GPTMS followed by hydrolysis to form GPTMS-OH | C$_2$-GPTMS-OH | 500 Å | 15° |
| 2 | bis(trichlorosilyl)ethane or bis(trimethoxysilyl)ethane | C$_2$ | 500 Å | 35° |

TABLE 1-continued

| VPD# | Vapor Deposited Material | Alternative Coating Abbreviation | Approximate Thickness of Product | Approximate Contact Angle |
|---|---|---|---|---|
| 3 | bis(trichlorosilyl)ethane or bis(trimethoxysilyl)ethane as a first layer followed by bis(trichlorosilyl)ethane or bis(trimethoxysilyl)ethane as a second layer. | $C_2-C_2$ | 1600 Å | 35° |
| 4 | bis(trichlorosilyl)ethane or bis(trimethoxysilyl)ethane as a first layer followed by GPTMS as a second layer | $C_2$-GPTMS | 500 Å | 50° |
| 5 | Annealed bis(trichlorosilyl)ethane or bis(trimethoxysilyl)ethane | Annealed $C_2$ | 500 Å | 95° |
| 6 | Annealed bis(trichlorosilyl)ethane or bis(trimethoxysilyl)ethane as a first layer followed by annealed bis(trichlorosilyl)ethane or bis(trimethoxysilyl)ethane as a second layer | Annealed $C_2-C_2$ | 1600 Å | 95° |
| 7 | bis(trichlorosilyl)ethane or bis(trimethoxysilyl)ethane as a first layer followed by n-decyltrichlorosilane as a second layer | $C_2C_{10}$ | 500 Å | 105° |
| 8 | Annealed bis(trichlorosilyl)ethane or bis(trimethoxysilyl)ethane as a first layer followed by annealed n-decyltrichlorosilane as a second layer | Annealed $C_2C_{10}$ | 500 Å | 105° |
| 9 | GPTMS | GPTMS | 100 to 200 Å | ~50° |
| 10 | GPTMS followed by hydrolysis to form GPTMS-OH | GPTMS-OH | 100 to 200 Å | ~20° |
| 11 | bis(trichlorosilyl)ethane or bis(trimethoxysilyl)ethane as a first layer followed by trimethylchlorosilane or trimethyldimethylaminosilane | $C_2C_3$ | 500 Å | 40-90° |
| 12 | annealed bis(trichlorosilyl)ethane or bis(trimethoxysilyl)ethane as a first layer followed by trimethylchlorosilane or trimethyldimethylaminosilane | Annealed $C_2C_3$ | 500 Å | 95° |
| 13 | bis(trichlorosilyl)ethane or bis(trimethoxysilyl)ethane as a first layer followed by a methoxy-polyethyleneoxy(3) propyl trichlorosilane or methoxy-polyethyleneoxy(3) propyl trimethoxysilane | $C_2$PEO | 500 Å | 15° |

Active Coatings

In addition to inert coatings, it is also beneficial to modify flow path components, including sample preparation devices and frits, with an organosilica (alkylsilyl) functionality that exhibits chemical properties that have an effect on the chromatographic separation. These so-called 'active' coatings can introduce a Coulombic repulsive effect with an analyte to shield them from interacting with the substrate material (e.g., metal, plastic, etc.) of the flow path in a way that negatively affects the chromatographic separation. In addition, an 'active' coating can be produced that adds an enhancing selectivity to a separation by way of a subtle secondary interaction. Moreover, an 'active' coating can be prepared that affords an entirely orthogonal retention mechanism, which facilitates the adsorption, partitioning, and desorption of analytes in a process distinct from that achieved with the stationary phase of a column. An active coating can also interact with the mobile phase to produce a desired effect on the chromatographic separation, for example, to enhance selectivity.

At least a portion of the surface of the sample preparation devices or frits are coated with an alkylsilyl coating having Formula IV:

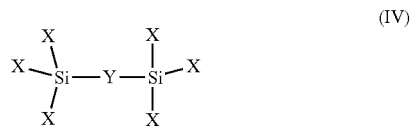

Each X of Formula IV is independently selected from $(C_1-C_6)$alkoxy, $—NH(C_1-C_6)$alkyl, $—N((C_1-C_6)$alkyl$)_2$, OH, $OR^A$, $R^B$, $R^C$, $R^D$ and halo. In some embodiments, X of Formula IV is independently selected from $OR^A$, $R^B$, $R^C$, and $R^D$. $(C_1-C_6)$alkoxy, $—NH(C_1-C_6)$alkyl, $—N((C_1-C_6)$alkyl$)_2$, OH, and halo are reactive/hydrolysable groups. In some embodiments, these groups provide residual reactive groups where amino>halo>alkoxy as it relates to silane reactivity. In some embodiments, the specific coating that is used (e.g., the specific selection of X in Formula IV) depends on the type of chromatographic separation being performed. The goal is to create chemically stable (good longevity) coatings on various materials present in a chromatographic flow path. However, hydrophilic coatings have no interactions in reversed phase liquid chromatography, while hydrophilic coatings can exhibit some retention in hydrophilic interaction chromatography. While one coating may suffice for multiple different chemical separations, different coatings can also be used for different modes of liquid chromatography.

$R^A$ represents a point of attachment to the surface of the sample preparation device and at least one X is $OR^A$. $R^B$ is absent or represents a hydrophobicity modifier. $R^C$ represents a charge modifier and at least one X is $R^C$. $R^D$ is absent, a chelator, or a crown ether. Y is a bridging moiety selected from $(C_1-C_{20})$alkyl, $—O[(CH_2)_2O]_{1-20}—$, $—(C_1-C_{10})[NH(CO)NH(C_1-C_{10})]_{1-20}$-, or $—(C_1-C_{10})[alkylphenyl(C_1-C_{10})alkyl]_{1-20}$-. The selection of Y can be dictated by both chemical and physical consideration.

Therefore, the alkylsilyl coating of Formula IV has at least one X that is $OR^A$, a point of attachment to the surface of the sample preparation device and at least one X that is $R^C$, which represents a charge modifier. The hydrophobicity modifier $R^B$ and the chelator or crown ether $R^D$ can be absent. In some embodiments, the alkylsilyl coating of Formula IV has a charge modifier. In some embodiments, the alkylsilyl coating of Formula IV has a charge modifier and a hydrophobicity modifier. In some embodiments, the alkylsilyl coating of Formula IV has a charge modifier and a chelator or crown ether. In some embodiments, the alkylsilyl coating of Formula IV has a charge modifier, a hydrophobicity modifier and a chelator or crown ether.

In other embodiments, the alkylsilyl coating of Formula IV has at least one X that is $OR^A$, a point of attachment to the surface of the sample preparation device and at least one X that is $R^D$, which represents a chelator or crown ether. In some embodiments, the alkylsilyl coating of Formula IV has a chelator or crown ether and a hydrophobicity modifier.

When used in the context of a chemical formula, a hyphen ("-") indicates the point of attachment. For example, when Y is —[(C$_1$-C$_{10}$)alkylphenyl(C$_1$-C$_{10}$)alkyl]$_{1-20}$-, that means that Y is connected to one SiX$_3$ via the (C$_1$-C$_{10}$)alkyl and connected to the other SiX$_3$ via the other (C$_1$-C$_{10}$)alkyl. This applies to the remaining variables.

In one embodiment, Y in Formula IV is (C$_1$-C$_{15}$)alkyl, (C$_1$-C$_{12}$)alkyl, or (C$_1$-C$_{10}$)alkyl. In some embodiments, Y in Formula IV is methyl, ethyl, propyl, isopropyl, butyl, sec-butyl, iso-butyl, t-butyl, pentyl, hexyl, heptyl, nonyl, or decanyl. In other aspect, Y in Formula IV is ethyl or decanyl.

In some embodiments, X of Formula IV can be another Y bridging moiety. In this way, the alkylsilyl coating can have more than two Si atoms bridged by two separated Y bridging moieties. When multiple Y bridging moieties are in the alkyl silyl coating, the Y bridging moieties can be the same Y moiety or different Y moieties. Multiple bridging moieties can result in the alkylsily coating being in a straight chain or branched. In addition, an alkylsilyl coating having multiple Y bridging moieties can be hyper-crosslinked with extensive bridging. The first bridging alkylsilyl composition can be highly crosslinked with some surface heterogeneity and mix of bridging moieties and silanols. That surface can then be modified with one or more of the modifiers described herein (e.g., charge modifiers, hydrophobicity modifiers, chelators and/or crown ethers, or surfactants).

In some embodiments, the active alkylsilyl coating is comprised at least in part by Formula IV as described herein. In that way, the alkylsilyl coating of Formula IV is at least a portion of the coating. The coating could have other Y bridging moieties with multiple modifiers as described herein.

In some embodiments a single modifier is used, for example, a single charge modifier. In other embodiments, multiple modifiers are used, for example, multiple charge modifiers or combinations of charge modifiers and hydrophobicity modifiers.

Charge Modifier (R$^C$)

Onto a suitable base layer, a charge modifying salinizing reagent can be applied. These charge bearing surface modifiers are comprised of strong acids/bases or weak acids/bases with a dissociation constant selected in a desirable range of pKa and can include but are not limited to trimethoxy silyl propyl methyl phosphonate and N,N-(diethylaminopropyl) trimethoxysilane. Surface modifiers with fixed charges, such as quaternary amines, can also be employed. For example for separation of nucleic acids or phosphopeptides that are negatively charged, the surface charge can be negative. In such case, the analytes are repelled from the surface and have no losses due to non-specific adsorption.

The charge modifier (R$^C$) can have the same charge as at least one analyte in the sample. When the charge modifier has the same charge as at least one analyte in the sample, the charge modifier introduces a Coulombic repulsive effect with the sample(s) having the same charge (i.e., like charges repel). For example, the analyte and the active coating can both be negatively charged. The analyte and the active coating can both be positively charged. This repulsive effect shields the analyte(s) from interacting with the substrate material of the flow path. The selection of an appropriate charge modifier can also depend on practical limitations, for example whether a suitable silane reagent can be sourced, or if it is to be synthesized, it is can be vaporized or made to be soluble in a suitable solvent system to carry out a reaction. In addition, the stability of the resulting coating should be considered. For example, a strong base that is also a nucleophile can be problematic because it can self-catalyze its hydrolytic degradation.

In addition to introducing a Coulombic repulsive effect with the sample(s) having the same charge, charge modifiers can also facilitate multidimensional chromatography by strongly retaining a class of analytes by a retention mechanism that is orthogonal to that of an implemented liquid chromatography column. For example, analytes adsorb to a flow path component having an alkylsilyl coating with a charge modifier (e.g., a frit at the entrance of a chromatography column), are eluted to a downstream chromatography column in a gradient or set of discrete mobile phase changes and secondary gradients across the packed bed of the chromatography column are thereafter performed. As another example, analytes adsorb to a sample preparation device having an alkylsilyl coating with a charge modifier.

The charge modifier can be, for example, any one or more of the following charge modifiers: a quaternary amine,

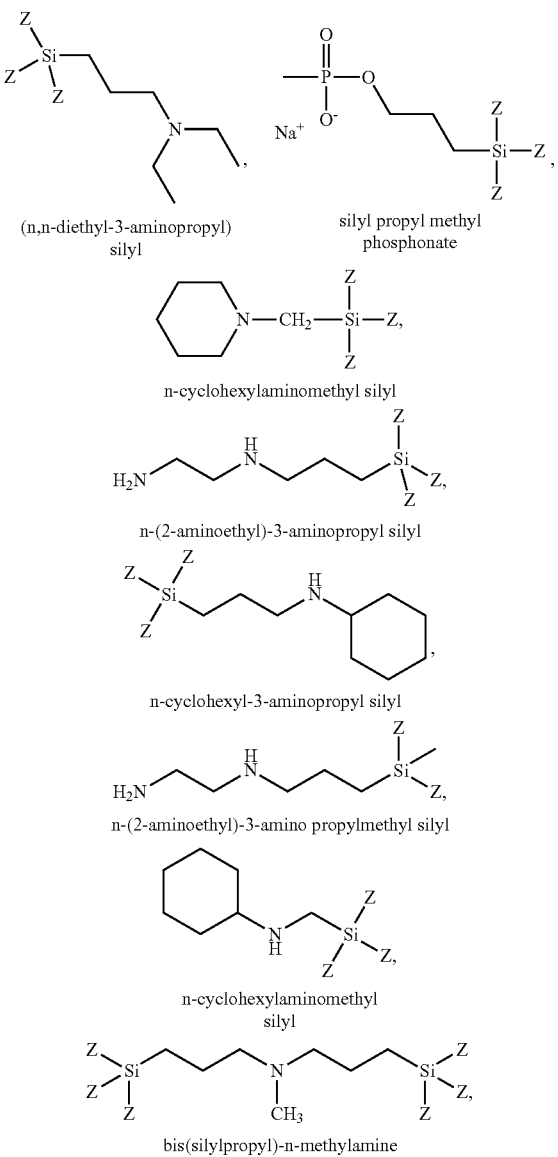

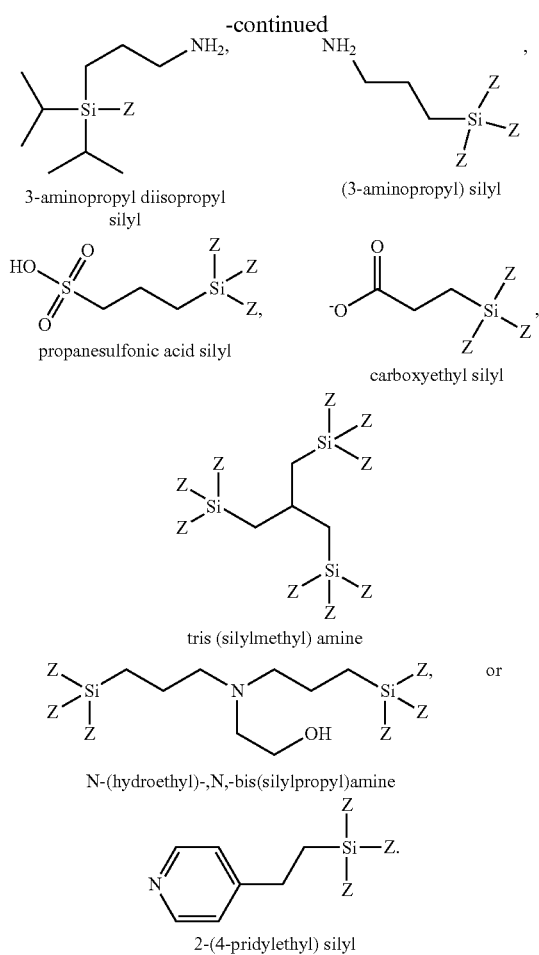

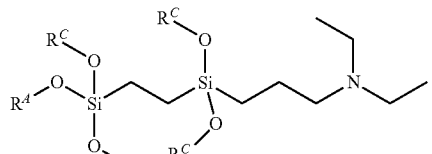

Z is independently selected from $(C_1-C_6)$alkoxy, —NH$(C_1-C_6)$alkyl, —N$((C_1-C_6)$alkyl$)_2$, OH, halo, or an attachment point to Formula IV. At least one Z is the attachment point to Formula IV. Therefore, the charge modifier is covalently bound to the alkylsilyl coating of Formula IV by a silyl ether moiety. A corresponding charge modifying reagent can be used to obtain the charge modifier of the final coating product, for example, the charge modifying reagent can be trimethoxy silyl propyl methyl phosphonate or N,N-(diethylaminopropyl) trimethoxysilane, or 2-(4-pyridylethyl)triethoxy silane.

In some embodiments a single charge modifier is applied to the vapor deposited alkylsilyl (Formula IV) coating. In other embodiments, multiple charge modifiers are applied to the vapor deposited alkylsilyl (Formula IV) coating. The multiple charge modifiers can be the same charge modifier applied at multiple X positions of Formula IV. Alternatively, the multiple charge modifiers can be different charge modifiers applied at different X positions of Formula IV.

In some embodiments, a vapor deposition alkylsilyl coating can be deliberately doped with a charged surface modifier ($R^C$), for example, the charged surface modifiers of U.S. Pat. No. 10,159,911 issued Dec. 25, 2018 and entitled "High Purity Chromatographic Materials Comprising an Ionizable Modifier," the entire contents of which is hereby incorporated by reference.

The charge modifier ($R^C$) can have a surface coverage of between about 0.01 µmol/m² to about 10 µmol/m². In some embodiments, the charge modifier ($R^C$) has a surface coverage of between about 0.02 µmol/m² to about 1 µmol/m². In some embodiment, the charge modifier ($R^C$) has a surface coverage of between about 0.1 µmol/m² to about 1 µmol/m².

An example of an active coating having an alkylsilyl coating of Formula IV with a charge modifier ($R^C$) that can result from coating #3 of FIG. 4 is shown below. Although the final alkylsilyl coating shown below has multiple points for other charge modifiers ($R^C$) those points could also be $(C_1-C_6)$alkoxy, —NH$(C_1-C_6)$alkyl, —N$((C_1-C_6)$alkyl$)_2$, OH, or a halo, as described herein. In addition, although the final alkylsilyl coating shown below has multiple points for other charge modifiers ($R^C$) those points could also be a hydrophobicity modifier ($R^B$) and/or chelators or crown ethers. The charge modifiers ($R^C$) shown below can also be other points of attachment to the surface of the sample preparation device, i.e., $R^A$.

Hydrophobicity Modifier ($R^B$)

In some embodiments, the alkysilyl coating with a charge modifier ($R^C$) is combined with a hydrophobicity modifier ($R^B$). The hydrophobicity modifier can have a net neutral charge. Encompassed within the reagent choices of a hydrophobicity modifier are zwitterionic modifiers, such as carboxy- and sulfobetaine reagents. A zwitterionic modifier affords a macroscopically, net neutral surface, but also lends microscopic Coulombic effects that can be repulsive to a wide range of analytes, including those with diverse charge characteristics.

The hydrophobicity modifier ($R^B$) can have a surface coverage between about 0.01 0.01 µmol/m² to about 10 µmol/m². In some embodiments, the hydrophobicity modifier ($R^B$) has a surface coverage of between about 0.03 µmol/m² to about 0.9 µmol/m². In some embodiments, the hydrophobicity modifier ($R^B$) has a surface coverage of between about 0.5 µmol/m² to about 3 µmol/m².

The hydrophobicity modifier ($R^B$) is attached to Formula IV by a silyl ether moiety and has a composition selected the from one or more of the following:

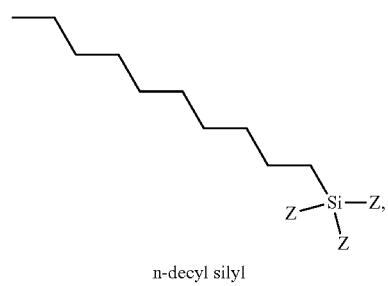

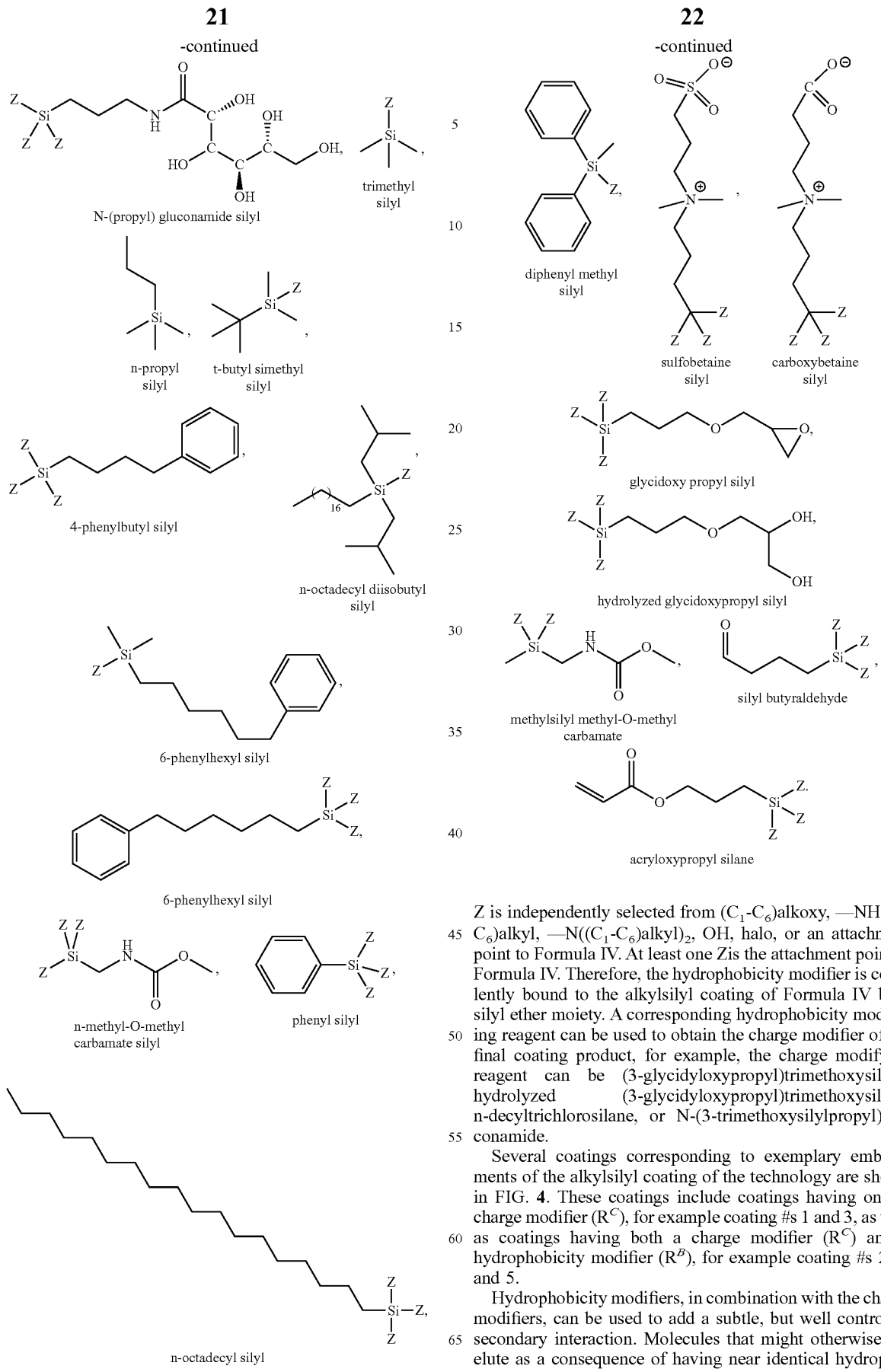

Z is independently selected from $(C_1-C_6)$alkoxy, —NH($C_1$-$C_6$)alkyl, —N(($C_1$-$C_6$)alkyl)$_2$, OH, halo, or an attachment point to Formula IV. At least one Z is the attachment point to Formula IV. Therefore, the hydrophobicity modifier is covalently bound to the alkylsilyl coating of Formula IV by a silyl ether moiety. A corresponding hydrophobicity modifying reagent can be used to obtain the charge modifier of the final coating product, for example, the charge modifying reagent can be (3-glycidyloxypropyl)trimethoxysilane, hydrolyzed (3-glycidyloxypropyl)trimethoxysilane, n-decyltrichlorosilane, or N-(3-trimethoxysilylpropyl)gluconamide.

Several coatings corresponding to exemplary embodiments of the alkylsilyl coating of the technology are shown in FIG. 4. These coatings include coatings having only a charge modifier ($R^C$), for example coating #s 1 and 3, as well as coatings having both a charge modifier ($R^C$) and a hydrophobicity modifier ($R^B$), for example coating #s 2, 4, and 5.

Hydrophobicity modifiers, in combination with the charge modifiers, can be used to add a subtle, but well controlled secondary interaction. Molecules that might otherwise coelute as a consequence of having near identical hydrophobicities can pass through, for example a frit coated with coating #4 shown in FIG. 4, where the molecule can experience subtle ion exchange partitioning when a gradient between water and acetonitrile based mobile phases are applied with acid modifiers of varying acidity, hydrophobicity, and ion pairing strength. Formic acid modified mobile phases are particularly useful in this regard as it does not attenuate electrostatic effects. This can be particularly useful when separating, for example, peptides, assays for citric acid cycle metabolites and glycans. Hydrophobicity modifiers, in combination with the charge modifiers, can also be used in hydrophilic interaction chromatography.

An example of an active coating having an alkylsilyl coating of Formula IV with a charge modifier ($R^C$) and a hydrophobicity modifier ($R^B$) that can result from coating #4 of FIG. 4 is shown below. Although the resulting coating shown below has multiple charge modifiers ($R^C$) any or all of those points could be a hydrophobicity modifier ($R^B$) or ($C_1$-$C_6$)alkoxy, —NH($C_1$-$C_6$)alkyl, —N(($C_1$-$C_6$)alkyl)$_2$, OH, or a halo or chelators or crown ethers, as described herein. In some embodiments, the charge modifier ($R^C$) and a hydrophobicity modifier ($R^B$) need not be directly linked, for example, the charge modifier ($R^C$) and a hydrophobicity modifier ($R^B$) can be connected through one or more bridging silicon moieties with Y (as defined herein) chemical compositions.

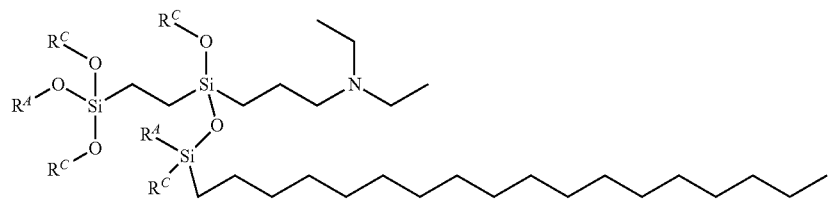

Chelators and Crown Ethers ($R^D$)

In some embodiments, the alkysilyl coating with a charge modifier ($R^C$) is combined with an ion scavenging ligand, for example a chelator or crown ether (i.e., $R^D$ is present). The chelator can be, for example, ethylenediaminetetraacetic acid or etidronic acid. The crown ether can be, for example, 18-crown-6, 12-crown-4, 15-crown-5, dibenzo-18-crown-6, or diaza-18-crown-6.

The chelators and crown ethers can be attached covalently to a silanized/alkylsilyl coating, either through direct covalent attachment or through the use of secondary linker moieties. The chelators and crown ethers can scavenge ions, for example, $Ca^{2+}$, $Fe^{3+}$ and/or $K^+$ that can be present in mobile phases, flow paths, and systems, which result in undesired gas phase ion adducts and cause the fouling and decommissioning of the mass spectrometer. For example, the chelator or crown ether can pull metal ions out of the mobile phase to improve MS spectra. Often, even MS grade mobile phases will contain trace amounts of metal ions, such as sodium and potassium, and it is common for the quality of the mass spectra to suffer, as a result. A 50 ppb concentration of potassium can yield a 2 to 10% relative intensity of potassiated adduct ion. An active coating such as this can sequester these metal ions, ensuring they are not present in the chromatographic effluent upon ionization. In turn, mass spectra can be obtained with ion adduct signals below 2% relative intensity even when mobile phases with questionable purity are employed. The use of chelators and crown ethers can be helpful when the technology is used in combination with a frit at the inlet of a chromatography column. While not limited to theory, it is believed to be possible to combine a chelator modified alkyl silane coating with an immobilized ligand so as to deplete certain ions from a sample. This can be taken advantage of to eliminate certain interferences with downstream detection or to facilitate a particular type of buffer exchange.

In some embodiments, the chelator and crown ethers can be combined directly with the alkylsilyl coating of Formula IV, without a charge modifier being present.

In some embodiments, the chelators and crown ethers can also be used in conjunction with the hydrophobicity modifiers described herein. In some embodiments, the chelators and crown ethers can be used in conjunction with both the charge modifiers and hydrophobicity modifiers described herein.

Therefore, when chelators and/or crown ethers are used as an active coating, a surface of a sample preparation device or a frit at the inlet of a chromatography column can be coated. At least a portion of the sample preparation device or the frit are coated with an alkylsilyl coating having the Formula IV:

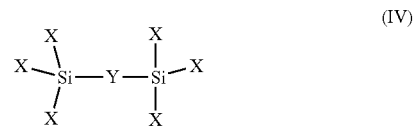

wherein each X is independently selected from ($C_1$-$C_6$) alkoxy, —NH($C_1$-$C_6$)alkyl, —N(($C_1$-$C_6$)alkyl)$_2$, OH, $OR^A$, $R^B$, $R^C$, $R^D$ and halo. $R^A$ represents a point of attachment to the interior surfaces of the sample preparation device or frit and at least one X is $OR^A$. $R^B$ is absent or represents a hydrophobicity modifier. $R^C$ is absent or represents a charge modifier. $R^D$ represents a chelator, or a crown ether, and at least one X is $R^D$. Y is a bridging moiety selected from ($C_1$-$C_{20}$)alkyl, —O[($CH_2$)$_2$O]$_{1-20}$—, —($C_1$-$C_{10}$)[NH(CO)NH($C_1$-$C_{10}$)]$_{1-20}$-, or —($C_1$-$C_{10}$)[alkylphenyl($C_1$-$C_{10}$)alkyl]$_{1-20}$-.

Bacteriostatic Modifiers

At least a portion of the surface of the sample preparation device or the frit at the inlet of a chromatography column are coated with an alkylsilyl coating having the Formula IV:

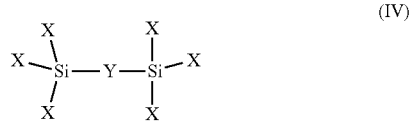

wherein each X is independently selected from $(C_1-C_6)$ alkoxy, $-NH(C_1-C_6)$alkyl, $-N((C_1-C_6)$alkyl$)_2$, OH, $OR^A$, $R^B$, $R^C$, $R^D$, $R^E$, and halo. $R^A$ represents a point of attachment to the surface of the sample preparation device or frit and at least one X is $OR^A$. $R^B$ is absent or represents a hydrophobicity modifier. $R^C$ is absent or represents a charge modifier. $R^D$ is absent or represents a chelator, or a crown ether. $R^E$ is a bacteriostatic moiety, and at least one X is $R^E$. Y is a bridging moiety selected from $(C_1-C_{20})$alkyl, $-O[(CH_2)_2O]_{1-20}-$, $-(C_1-C_{10})[NH(CO)NH(C_1-C_{10})]_{1-20}-$, or $-(C_1-C_{10})[alkylphenyl(C_1-C_{10})alkyl]_{1-20}-$.

In some embodiments, the bacteriostatic moiety is a zwitterion. The zwitterionic coatings can be prepared by silanization with bis(trichlorosilyl)ethane followed by derivatization with N,N-(diethylaminopropyl)trimethoxysilane and subsequent reactions with chloro or bromo alkylcarboxylic acids. In some embodiments, the bacteriostatic moiety is a quaternary amine.

The bacteriostatic moiety can be used alone, or in conjunction with a charge modifier, a hydrophobicity modifier and/or a chelator or crown ether.

Surfactants

In some embodiments, surfactants can be used as an active coating to solubilize proteins, including hydrophobic membrane proteins, and provide a denaturing environment that facilitates enzyme reactions, such as proteolysis and glycan release.

At least a portion of the surface of the sample preparation device or the frit are coated with an alkylsilyl coating having the Formula IV:

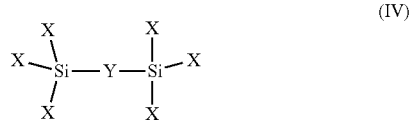

wherein each X is independently selected from $(C_1-C_6)$ alkoxy, $-NH(C_1-C_6)$alkyl, $-N((C_1-C_6)$alkyl$)_2$, OH, $OR^A$, $R^B$, $R^C$, $R^D$, $R^E$, $R^F$, and halo. $R^A$ represents a point of attachment to the surface of the sample preparation device or frit and at least one X is $OR^A$. $R^B$ is absent or represents a hydrophobicity modifier. $R^C$ is absent or represents a charge modifier. $R^D$ is absent or represents a chelator, or a crown ether. $R^E$ is absent or represents a bacteriostatic moiety. $R^F$ represents a surfactant, and at least one X is $R^F$. Y is a bridging moiety selected from $(C_1-C_{20})$alkyl, $-O[(CH_2)_2O]_{1-20}-$, $-(C_1-C_{10})[NH(CO)NH(C_1-C_{10})]_{1-20}-$, or $-(C_1-C_{10})[alkylphenyl(C_1-C_{10})alkyl]_{1-20}-$.

In some embodiments, the surfactant ($R^F$) is sodium dodecyl sulfate, zwittergent 3-10 (Decyldimethylammonio) propanesulfonate, sodium deoxycholate, hexadecyl trimethyl ammonium bromide, triton, polysorbate, or a combination thereof. In some embodiments, a surface is modified to have a coverage of alkylsilyl coating wherein one region is modified to bear the immobilized biological ligand while another exhibits an immobilized surfactant that can facilitate the denaturation of a protein analyte. In practice, this surface can then be used to initiate the denaturation of the protein analyte while also priming it for being acted upon by a biological ligand, such as a protease, including, but not limited to, trypsin.

Biological Ligands

An alkylsilyl coating, as described herein, can be modified with a biological ligand, for example, an affinity ligand or an enzyme, thus creating off-line and on-line LC sample preparation devices of noteworthy utility. A device that contains an alkylsilyl coating and an immobilized biological ligand, has a surface coverage of the biological ligand (i.e., either an affinity ligand or an enzyme) ranging from about 1 to about 1000 nmol/m², more specifically about 2 to about 500 nmol/m². The devices having an alkylsilyl coating and an immobilized biological ligand can be employed to perform sample preparation for a subsequent LC based assay, including either the enrichment of an analyte or its conversion into a constituent that can be more easily or more selectively detected. Analyses facilitated with this technology can also include capillary electrophoresis and mass spectrometry.

Affinity Ligands

An alkylsilyl coating, as described above, can be modified with a biological ligand, for example, an affinity ligand, thus creating off-line and on-line LC sample preparation devices of noteworthy utility.

With this technology, deposited alkylsilyl surfaces, as described above, are further modified to bear immobilized affinity ligands that are capable of facilitating analyte sample preparation steps to facilitate an LC-MS assay. Affinity chromatography is used in countless assays to capture analytes, enhance selectivity and improve limits of detection. Affinity capture is a starting point to the analysis of biologics produced by cell culture and the analysis of biotherapeutics circulating in patient biofluids. Among the various options, this coating be comprised of covalently attached antibodies, single domain antibodies, aptamers, affimers, streptavidin, protein A, protein G, protein L or a combination thereof. These ligands can be attached directly to the silanized/alkylsilyl coating, as is possible via reductive amination, NHS activated electrophilic substitution, carbodiimide dehydration or a Michael addition reaction. In some embodiments, a spacer molecule (or linker) is used to link the affinity ligand to the coating. For instance, a protein ligand containing a free thiol can be linked to a coating through silanization and secondary reaction with a maleimide PEG silane, wherein the PEG repeat can range from 3 to 300 (see below). Alternatively, an amino silane modified coating can be combined with an NHS activated maleimide PEG to achieve the same end. As well, an amino silane modified surface can be combined with bis-aldehyde reagents (such as glutaraldehyde or a PEG dialdehyde) and reductive amination to afford immobilizations that bridge the amine surface to the amine functional groups of a biological ligand. In addition, a coating can be modified with a acryloxy silane, which can then be used for a Michael addition type immobilization of the biological ligand.

Examples of spacer molecules (or linkers) are shown below where n is from 3 to 300.

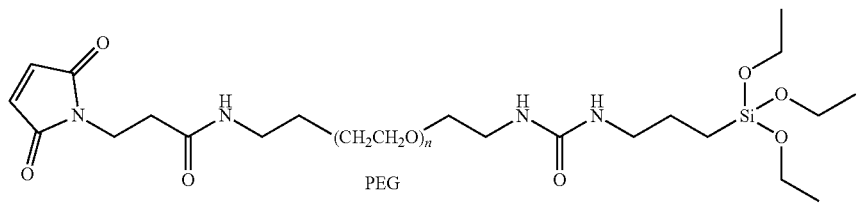

Maleimide PEG Silane

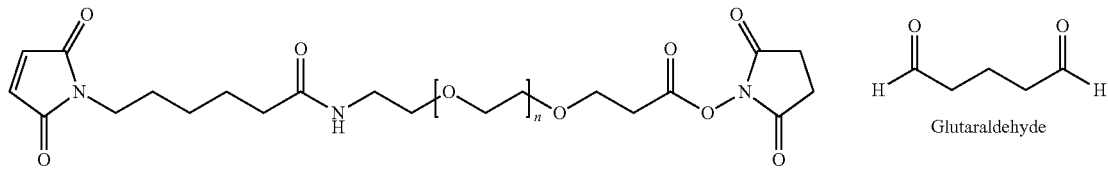

NHS PEG Maleimide

Glutaraldehyde

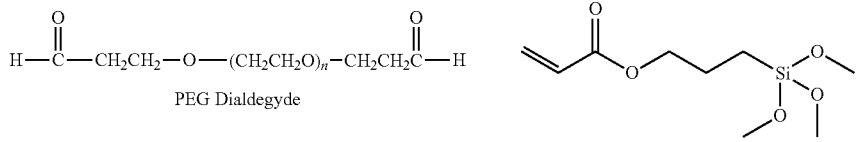

PEG Dialdegyde

Acryloxy Silane

A selection of exemplary biological ligands are provided below. One example exhibits a single amino acid residue sequence of a camelid single domain antibody that can be used for selective capture of human immunoglobulin Fe domains. With this ligand, a C-terminal cysteine residue exists so as to facilitate oriented conjugation. For a second example, the sequence of a nucleic acid aptamer is provided. This aptamer also displays affinity for human immunoglobulin Fc domains. It is shown as an amino-terminated 5' construct through which it is possible to perform site directed conjugation via reductive amination. In yet another example, a sequence of porcine trypsin is provided, which can be used for protein digestion. FIGS. 5A-5C summarizes several examples of coatings and immobilized biological ligands that can be prepared using the above mentioned constituents.

Sequence of a Camelid VHH Single Domain Antibody for the Capture of Human Immunoglobulin Fc Domains (Amino Acid):

```
                                        (SEQ ID NO: 1)
QVQLQESGGGLVQPGGSLRSCAASGGTSIRIGSINALAWYRQALGNQREL

VAAVTEGGSTNYADFVKGRFTISRDQAQNMMYLQMNSLKPEDTAVYYCNA

DKVLYSRGGYYSVANDLWGQGTQVTVSSQAPKVDAKFDC
```

Sequence of a Nucleic Acid Aptamer for the Capture of Human Immunoglobulin Fc Domains (Nucleic Acid):

```
                                        (SEQ ID NO: 2)
5' amino-GGrArGrGfUrGCfUCCGAAArGrGAAfCfUCC
``` where G stands for 2' deoxy guanosine, rA for 2' hydroxyadenine, rG for 2' hydroxyguanosine, U denotes 2'-Fluoro-2'-deoxyuridine, C for 2' deoxy cytidine, A for 2' deoxy adenine, and 5' amino for a 5' modification consisting of a primary amino group.

In some embodiments, the affinity ligand has the sequence depicted in SEQ ID NO: 1. The affinity ligand can be at least 75%, 76%, 77%, 78%, 79% 80%, 81%, 82%, 83%, 84%. 85%, 86%, 87%, 88%, 89%, 90%, 91%, 92%, 93%, 94%, 95%, 96%, 97%, 98%, or 99% identical to the sequence depicted in SEQ ID NO: 1.

In some embodiments, the affinity ligand has the sequence depicted in SEQ ID. NO: 2. The affinity ligand can be at least 75%, 76%, 77%, 78%, 79% 80%, 81%, 82%, 83%, 84%. 85%, 86%, 87%, 88%, 89%, 90%, 91%, 92%, 93%, 94%, 95%, 96%, 97%, 98%, or 99% identical to the sequence depicted in SEQ ID NO: 2.

Affinity Ligand Methods

The technology also includes methods of analyzing a biofluid using an affinity ligand immobilized on an alkylsilyl coated substrate (e.g., a sample preparation device). The method includes providing a sample preparation device, for example, any one of the sample preparation devices having an affinity ligand immobilized on an alkylsilyl coated surface of the sample preparation device. The method also includes aspirating the biofluid comprising an analyte onto the surface of the sample preparation device to form an affinity complex such that the analyte is adsorbed. The adsorbed analyte is washed with a neutral, isotonic buffer. The adsorbed analyte is eluted from the surface of the sample preparation device. The eluted sample is then analyzed using liquid chromatography, mass spectrometry, ELISA, capillary electrophoresis, or a combination thereof.

The affinity ligand used in the method can be any affinity ligand described herein. The affinity ligand can be capable of capturing human immunoglobulin Fc domains. For example, a single acid residue sequence of a camelid single domain antibody can be used for the selective capture of human immunoglobulin Fc domains. A nucleic acid aptamer also displays affinity for human immunoglobulin Fc domains.

In another embodiment, a method of separating a biofluid is provided using an affinity ligand immobilized on an alkylsilyl coated substrate (e.g., a frit). The method includes providing a frit located at an inlet of a chromatography column. The frit has an affinity ligand immobilized on an alkylsilyl coated surface of the frit, e.g., any of the coatings having an immobilized affinity ligand described herein. The biofluid comprising an analyte is loaded onto the surface of the frit. The analyte is captured to form an affinity complex such that the analyte is adsorbed on the surface of the frit while a remainder of the biofluid passes through the chromatography column. The adsorbed analyte is eluted from the surface of the frit such that the analyte passes through the chromatography column. The analyte is then detected by a detector.

The chromatography column can be a size exclusion chromatography (SEC) column. The detector can be a mass spectrometer. The biofluid can be a humanized mAb based therapeutic. The affinity ligand can be an anti-human Fc aptamer, an anti-human Fc immunoglobulin antibody, an anti-human Fc single domain antibody ligand, or a combination thereof.

When separating a biological sample, the alkylsilyl coating and affinity ligand can each provide a desired effect on the overall separation. For example, when separating a sample comprising a biofluid, an affinity ligand can be used to form an affinity complex with an analyte in the sample while the alkylsilyl coating can ensure that other analytes in the sample are not adsorbed onto a surface of the sample preparation device (e.g., due to interactions with a metal substrate) and are therefore not eluted with the analyte forming an affinity complex with the affinity ligand. In this way, an inert alkylsilyl coating along with an affinity ligand beneficially reduces adsorption of analytes on a substrate while the affinity ligand selectively adsorbs a specific analyte that can be later eluted and detected.

Enzymes

An alkylsilyl coating, as described above, can be modified with a biological ligand, for example, an enzyme, that are helpful to the analysis of samples. These enzymes can be selected from proteases, glycosidases, ligases, transferases, oxidoreductases, isomerases, hydrolases or a combination thereof. Proteases of significance to peptide mapping, IdeS and IdeZ for fragmentation of antibodies, glycosidases useful for O- and N-glycan profiling, carboxypeptidases, and nucleases could all be used to afford different embodiments of this invention. In some cases, a mixture of enzymes can be immobilized to achieve a single pot reaction and more than one chemical conversion. Alternatively, this technology can comprise a β-glucuronidase enzyme for facilitating the analysis of opioid glucuronides. These can be made to be part of an offline sample preparation device or to create a sample preparation machine or a dedicated, all-in-one LC-MS analyzer. In some aspects, these immobilized-enzyme coated surfaces can be prepared and used with an LC system to make a protein digestion apparatus or analyzer useful for the peptide mapping of protein therapeutics.

The enzymes can be, for example, trypsin, Lys-C, Arg-C, Lys-N, Glu-C, Asp-N, pepsin, Ides, IdeZ, IgdE, Gingipain K, PNGase F, or combinations thereof.

Below is an example of a sequence of beta-glucuronidase are provided, which can be used for hydrolysis of opioid metabolites. FIGS. 5A-5C summarizes several examples of coatings and immobilized biological ligands that can be prepared using the above mentioned constituents.

Sequence of Porcine Trypsin, a Protease for Protein Digestion (Amino Acid):

```
                                               (SEQ ID NO: 3)
IVGGYTCAANSIPYQVSLNSGSHFCGGSLINSQWVVSAAHCYKSRIQVRL

GEHNIDVLEGNEQFINAAKIITHPNFNGNTLDNDIMLIKLSSPATLNSRV

ATVSLPRSCAAAGTECLISGWGNTKSSGSSYPSLLQCLKAPVLSDSSCKS

SYPGQITGNMICVGFLEGGKDSCQGDSGGPVVCNGQLQGIVSWGYGCAQK

NKPGVYTKVCNYVNWIQQTIAAN
```

Sequence of Beta-Glucuronidase for the Hydrolysis of Opioid Metabolites (Amino Acid):

```
                                               (SEQ ID NO: 4)
GLQGGMLYPQESPSRECKELDGLWSFRADFSDNRRRGFEEQWYRRPLWES

GPTVDMPVPSSFNDISQDWRLRHFVGWVWYEREVILPERWTQDLRTRVVL

RIGSAHSYAIVWVNGVDTLEHEGGYLPFEADISNLVQVGPLPSRLRITIA

INNTLTPTTLPPGTIQYLTDTSKYPKGYFVQNTYFDFFNYAGLQRSVLLY

TTPTTYIDDITVTTSVEQDSGLVNYQISVKGSNLFKLEVRLLDAENKVVA

NGTGTQGQLKVPGVSLWWPYLMHERPAYLYSLEVQLTAQTSLGPVSDFYT

LPVGIRTVAVTKSQFLINGKPFYFHGVNKHEDADIRGKGFDWPLLVKDFN

LLRWLGANAFRTSHYPYAEEVMQMCDRYGIVVIDECPGVGLALPQFFNNV

SLHHHMQVMEEVVRRDKNHPAVVMWSVANEPASHLESAGYYLKMVIAHTK

SLDPSRPVTFVSNSNYAADKGAPYVDVICLNSYYSWYHDYGHLELIQLQL

ATQFENWYKKYQKPIIQSEYGAETIAGFHQDPPLMFTEEYQKSLLEQYHL

GLDQKRRKYVVGELIWNFADFMTEQSPTRVLGNKKGIFTRQRQPKSAAFL

LRERYWKIANETRYPHSVAKSQCLENSLFT
```

In some embodiments, the enzyme has the sequence depicted in SEQ ID NO: 3. The enzyme can be at least 75%, 76%, 77%, 78%, 79% 80%, 81%, 82%, 83%, 84%. 85%, 86%, 87%, 88%, 89%, 90%, 91%, 92%, 93%, 94%, 95%, 96%, 97%, 98%, or 99% identical to the sequence depicted in SEQ ID NO: 3.

In some embodiments, the enzyme has the sequence depicted in SEQ ID. NO: 4. The enzyme can be at least 75%, 76%, 77%, 78%, 79% 80%, 81%, 82%, 83%, 84%. 85%, 86%, 87%, 88%, 89%, 90%, 91%, 92%, 93%, 94%, 95%, 96%, 97%, 98%, or 99% identical to the sequence depicted in SEQ ID NO: 4.

Enzyme Methods

The technology also includes methods for quantifying opioid glucuronides using a sample preparation device that has a surface having an alkylsilyl coating (as described herein) with an immobilized β-glucuronidase enzyme. A sample comprising the opioid glucuronides is aspirated onto the surface of the sample preparation device such that the opioid glucuronides is hydrolyzed. The hydrolyzed opioid glucuronides is recovered from the surface of the sample preparation device. The recovered hydrolyzed opioid glucuronides is injected onto a liquid chromatography column.

The technology also includes methods for preparing a sample comprising a protein for peptide mapping using a sample preparation device that has a surface having an alkylsilyl coating (as described herein) with an immobilized protease enzyme. The protease enzyme can be trypsin, Lys-C, Arg-C, Lys-N, Glu-C, Asp-N, pepsin, or a combination thereof. The sampel comprising the protein can be aspirated onto the surface of the sample preparation device such that the protein is digested into peptide fragments. The peptide fragments are recovered from the sample preparation device and injected onto a liquid chromatography column. In some embodiments, the protease enzyme is trypsin, Lys-C, Asp-N or a combination thereof.

In some embodiments, the alkylsilyl coating is bis(trichlorosilyl)ethane and the protease enzyme is trypsin, wherein the trypsin is covalently bonded to the bis(trichlorosilyl)ethane by a maleimide PEG silane linker (e.g., #5 of FIGS. 5A-5C). The maleimide PEG silane linker can be:

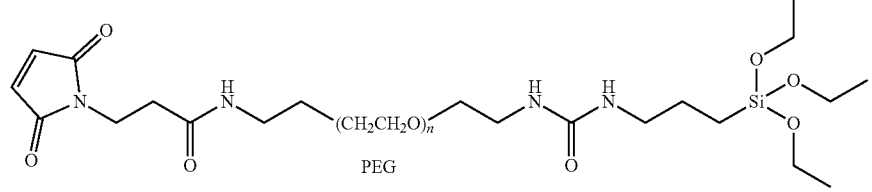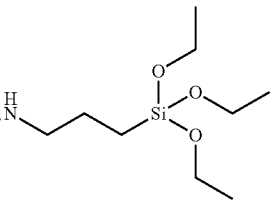

wherein n is between 3 and 300.

The alkylsilyl coating can be bis(trichlorosilyl)ethane modified with triethoxysilyl butyraldehyde and the protease enzyme can be trypsin, wherein the trypsin is covalently bonded to the triethoxysilyl butyraldehyde modified bis(trichlorosilyl)ethane by reductive amination (e.g., #6 of FIGS. 5A-5C).

In some embodiments, the alkylsilyl coating is bis(trichlorosilyl)ethane modified with 3-aminopropyl trimethoxysilane and the protease enzyme is trypsin, wherein the trypsin is covalently bonded to the 3-aminopropyl trimethoxysilane modified bis(trichlorosilyl)ethane by reductive amination with a PEG dialdehyde (e.g., #7 of FIGS. 5A-5C). The PEG dialdehyde can be:

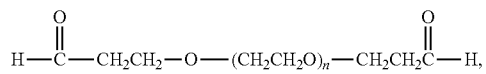

wherein n is between 3 and 300.

In some embodiments, the alkylsilyl coating is bis(trichlorosilyl)ethane modified with triethoxysilyl butyraldehyde and acrylate PEG amine, and the protease enzyme is trypsin, wherein the trypsin is covalently bonded to the modified bis(trichlorosilyl)ethane by reductive amination and Michael addition (e.g., #8 of FIGS. 5A-5C). The acrylate PEG amine can be:

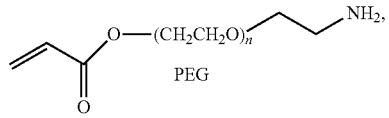

wherein n is between 3 and 300.

In some embodiments, the alkylsilyl coating is bis(trichlorosilyl)ethane modified with acryloxypropyltrimethoxy silane and the protease enzyme is trypsin, wherein the trypsin is covalently bonded to the acryloxypropyltrimethoxy silane modified bis(trichlorosilyl)ethane by Michael addition (e.g., #9 of FIGS. 5A-5C).

The technology also includes a method of analyzing a sample comprising monoclonal antibodies (mAb) using a sample preparation device that has a surface having an alkylsilyl coating (as described herein) with an immobilized enzyme covalently bonded to the alkylsilyl coating. The enzyme is IdeS, IdeZ, IgdE, Gingipain K or a combination thereof. The sample comprising the mAb is aspirated onto the surface of the sample preparation device such that the mAb is fragmented into subunits. The subunits of the mAb are recovered from the sample preparation device and injected onto a liquid chromatography column.

The technology also includes a method of analyzing a sample comprising a glycoprotein, using a sample preparation device that has a surface having an alkylsilyl coating (as described herein) with an immobilized PNGase F enzyme. The sample comprising the glycoprotein is aspirated onto the surface of the sample preparation device such that the glycans of the glycoprotein are cleaved. The deglycosylated glycoprotein is recovered from the sample preparation device injected onto a liquid chromatography column.

When separating a biological sample, the alkylsilyl coating and enzyme can each provide a desired effect on the overall separation. For example, when separating a sample comprising a biofluid, an enzyme can be used to, for example, hydrolyze or digest an analyte in the sample while the alkylsilyl coating can ensure that the produced digest products are not adsorbed onto a surface of the sample preparation device (e.g., due to interactions with a metal substrate) and are therefore recovered in high yield. In this way, an inert alkylsilyl coating along with an enzyme beneficially reduces adsorption of analytes on a substrate while the enzyme selectively interacts with a specific analyte that can be later recovered and detected.

EXAMPLES

Example 1—Sample Prep with a Microelution Plate Having an Affinity Surface

In one example of this technology, a 96 well microelution plate, tapered bottom vial, or pipette tip is coated with bis(trichlorosilyl)ethane and secondarily modified to bear an affinity ligand for capturing human immunoglobulin Fc domains, including but not limited to a nucleic acid aptamer (SEQ ID NO: 2), immunoglobulin or single domain VHH camelid antibody (SEQ ID NO: 1). A biofluid is aspirated onto the surface and allowed to equilibrate such that an affinity complex forms. The adsorbed analyte is washed with a neutral, isotonic buffer and then eluted with eluent. The resulting analyte is thereafter injected onto and separated across a liquid chromatography column.

Example 2—Online MS with an Immobilized Affinity Surface

In yet another example, this technology can be employed as a component of an LC flow path. A 0.2 μm porosity stainless steel frit can be modified with bis(trichlorosilyl) ethane coating and immobilization reactions with an anti-human Fc aptamer (SEQ ID NO: 2). This frit can be used as the inlet of a size exclusion (SEC) column, including but not limited to an ACQUITY® UPLC® BEH SEC 200 Å 1.7 μm column (commercially available from Waters Technologies Corporation, Milford, MA). Onto this apparatus, a biofluid sample containing a humanized mAb based therapeutic can be loaded. The inlet frit, with its coating, would thereby selectively capture the therapeutic while sample matrix would pass through the column apparatus. Subsequently, the adsorbed mAb based therapeutic would be desorbed with an injection of eluent. The SEC mobile phase composition would be selected to be comprised of volatile components. The desorbed therapeutic would elute in a minimal peak volume and traverse the SEC column to be detectable by mass spectrometry. Non-volatile eluent from the injection would be shunted to waste. Optionally, this immobilized affinity ligand apparatus can be used without a secondary chromatographic technique. In some embodiments, it can be constructed with an anti-human Fc immunoglobulin antibody or an anti-human Fc single domain antibody ligand. In these latter cases, elution of the captured analyte can be facilitated by a low pH, volatile eluent.

SEQUENCE LISTING TABLE

| SEQ ID | DESCRIPTION | SEQUENCE |
|---|---|---|
| 1 | Camelid VHH Single Domain Antibody (amino acid) | QVQLQESGGGLVQPGGSLRSCAASGGTSIRIGSINALAWYRQALGN QRELVAAVTEGGSTNYADFVKGRFTISRDQAQNMMYLQMNSLKPE DTAVYYCNADKVLYSRGGYYSVANDLWGQGTQVTVSSQAPKVDA KFDC |
| 2 | Aptamer (nucleic acid) | 5' amino-GGrArGrGfUrGCfUCCGAAArGrGAAfCfUCC where G stands for 2' deoxy guanosine, rA for 2' hydroxyadenine, rG for 2' hydroxyguanosine, fU denotes 2'-Fluoro-2'-deoxyuridine, C for 2' deoxy cytidine, A for 2' deoxy adenine, and 5' amino for a 5' modification consisting of a primary amino group. |
| 3 | Porcine Trypsin (amino acid) | IVGGYTCAANSIPYQVSLNSGSHFCGGSLINSQWVVSAAHCYKSRIQ VRLGEHNIDVLEG NEQFINAAKIITHPNFNGNTLDNDIMLIKLSSPATLNSRVATVSLPRS CAAAGTECLISG WGNTKSSGSSYPSLLQCLKAPVLSDSSCKSSYPGQITGNMICVGFLE GGKDSCQGDSGGP VVCNGQLQGIVSWGYGCAQKNKPGVYTKVCNYVNWIQQTIAAN |
| 4 | Beta-Glucuronidase (amino acid) | GLQGGMLYPQESPSRECKELDGLWSFRADFSDNRRRGFEEQWYRR PLWESGPTVDMPVPSSFNDISQDWRLRHFVGWVWYEREVILPERW TQDLRTRVVLRIGSAHSYAIVWVNGVDTLEHEGGYLPFEADISNLV QVGPLPSRLRITIAINNTLTPTTLPPGTIQYLTDTSKYPKGYFVQNTYF DFFNYAGLQRSVLLYTTPTTYIDDITVTTSVEQDSGLVNYQISVKGS NLFKLEVRLLDAENKVVANGTGTQGQLKVPGVSLWWPYLMHERP AYLYSLEVQLTAQTSLGPVSDFYTLPVGIRTVAVTKSQFLINGKPFY FHGVNKHEDADIRGKGFDWPLLVKDFNLLRWLGANAFRTSHYPYA EEVMQMCDRYGIVVIDECPGVGLALPQFFNNVSLHHHMQVMEEVV RRDKNHPAVVMWSVANEPASHLESAGYYLKMVIAHTKSLDPSRPV TFVSNSNYAADKGAPYVDVICLNSYYSWYHDYGHLELIQLQLATQF ENWYKKYQKPIIQSEYGAETIAGFHQDPPLMFTEEYQKSLLEQYHL GLDQKRRKYVVGELIWNFADFMTEQSPTRVLGNKKGIFTRQRQPKS AAFLLRERYWKIANETRYPHSVAKSQCLENSLFT |

The invention claimed is:

1. A sample preparation device for enriching a component of a sample, the sample preparation device comprising:
   a surface in fluid communication with the sample;
   an alkylsilyl coating disposed on the surface, wherein the alkylsilyl coating comprises a vapor deposited product of bis(trichlorosilyl)ethane or bis(trimethoxysilyl)ethane; and
   an affinity ligand or an enzyme covalently bonded to the alkylsilyl coating, wherein the surface is an interior surface of a well plate.

2. The sample preparation device of claim 1, wherein the sample preparation device is used for chromatographic analysis.

3. The sample preparation device of claim 1, wherein the sample preparation device is used for mass spectrometric analysis.

4. The sample preparation device of claim 1, wherein the alkylsilyl coating is selected to interact with at least one analyte in the sample through (1) a repulsive force, (2) a secondary interaction, or (3) a retention mechanism distinct from the interaction with a stationary phase material.

5. The sample preparation device of claim 1, wherein the affinity ligand is an antibody, a single domain antibody, an aptamer, an affimer, streptavidin, protein A, protein G, or protein L, or a combination thereof.

6. The sample preparation device of claim 1, further comprising a linker to covalently bond the affinity ligand to the alkylsilyl coating.

7. The sample preparation device of claim 6, wherein the linker is a maleimide PEG silane, an NHS PEG Maleimide, or PEG dialdehyde, where the PEG repeat is between 3 and 300.

8. The sample preparation device of claim 6, wherein the linker is glutaraldehyde or acryloxysilane.

9. The sample preparation device of claim 1, wherein the covalent bond between the affinity ligand and the alkylsilyl coating is made through reductive amination.

10. The sample preparation device of claim 1, wherein the affinity ligand has a surface coverage of about 1 to about 1000 nmol/m$^2$.

11. The sample preparation device of claim 1, wherein the affinity ligand has a surface coverage of about 2 to about 500 nmol/m$^2$.

12. The sample preparation device of claim 1, wherein the enzyme is selected from proteases, glycosidases, ligases, transferases, oxidoreductases, isomerases, hydrolases, or a combination thereof.

13. The sample preparation device of claim 12, wherein the enzyme is a protease and the protease is selected from IdeS, IdeZ, or a combination thereof.

14. The sample preparation device of claim 1, wherein the enzyme is β-glucuronidase.

15. The sample preparation device of claim 1, wherein the enzyme has a surface coverage of about 1 to about 1000 nmol/m$^2$.

16. The sample preparation device of claim 1, wherein the enzyme has a surface coverage of about 2 to about 500 nmol/m$^2$.

* * * * *